(12) United States Patent
Rezac et al.

(10) Patent No.: US 9,308,349 B2
(45) Date of Patent: Apr. 12, 2016

(54) UNIVERSAL CATHETER HANDLE

(71) Applicant: Vention Medical Advanced Components, Inc., Salem, NH (US)

(72) Inventors: David A. Rezac, Westborough, MA (US); Keith D. Boudreau, Beverly, MA (US); Alan Fortunate, Boston, MA (US)

(73) Assignee: Vention Medical Advanced Components, Inc., Salem, NH (US)

( * ) Notice: Subject to any disclaimer, the term of this patent is extended or adjusted under 35 U.S.C. 154(b) by 99 days.

(21) Appl. No.: 14/169,420

(22) Filed: Jan. 31, 2014

(65) Prior Publication Data

US 2014/0228800 A1 Aug. 14, 2014

Related U.S. Application Data

(60) Provisional application No. 61/901,650, filed on Nov. 8, 2013, provisional application No. 61/763,111, filed on Feb. 11, 2013, provisional application No. 61/762,436, filed on Feb. 8, 2013.

(51) Int. Cl.
| | |
|---|---|
| *A61M 25/00* | (2006.01) |
| *A61M 25/01* | (2006.01) |
| *A61F 2/95* | (2013.01) |
| *A61M 25/09* | (2006.01) |

(52) U.S. Cl.
CPC ....... *A61M 25/0136* (2013.01); *A61M 25/0147* (2013.01); *A61F 2002/9517* (2013.01); *A61M 2025/09116* (2013.01); *Y10T 29/49826* (2015.01)

(58) Field of Classification Search
CPC ............ A61F 2002/9517; A61M 2025/09116; A61M 25/0136; A61M 25/0147; A61M 25/0133; A61M 2025/015
See application file for complete search history.

(56) References Cited

U.S. PATENT DOCUMENTS

| | | | | |
|---|---|---|---|---|
| 5,114,403 | A | * 5/1992 | Clarke | A61M 25/01 604/95.04 |
| 5,254,088 | A | 10/1993 | Lundquist et al. | |
| D347,473 | S | 5/1994 | Nitzsche | |
| 5,391,172 | A | 2/1995 | Williams et al. | |
| 5,433,723 | A | * 7/1995 | Lindenberg | A61F 2/88 606/198 |
| 5,906,619 | A | * 5/1999 | Olson | A61F 2/95 606/108 |
| 6,027,462 | A | * 2/2000 | Greene | A61M 25/0136 600/585 |
| 6,171,277 | B1 | 1/2001 | Ponzi | |

(Continued)

FOREIGN PATENT DOCUMENTS

| | | |
|---|---|---|
| EP | 1117341 | 7/2001 |
| EP | 1358903 | 5/2003 |
| EP | 1942975 | 7/2009 |

OTHER PUBLICATIONS

Bard, "Radia XT" (http://www.bardep.com/pdf/BAW04Z0650.pdf).

(Continued)

*Primary Examiner* — Nathan R Price
*Assistant Examiner* — William Carpenter
(74) *Attorney, Agent, or Firm* — Onello & Mello, LLP; David Silverstein

(57) ABSTRACT

A catheter actuation handle apparatus is disclosed that is designed and configured for manipulating one or more distally-extending members to achieve translation, articulation and/or rotation of these members using the actuation handle.

52 Claims, 27 Drawing Sheets

(56) References Cited

U.S. PATENT DOCUMENTS

| | | | |
|---|---|---|---|
| 6,464,645 B1* | 10/2002 | Park | A61B 1/0052 600/462 |
| 6,783,521 B2 | 8/2004 | Ponzi et al. | |
| 6,805,675 B1* | 10/2004 | Gardeski | A61M 25/0136 600/585 |
| 7,105,016 B2* | 9/2006 | Shiu | A61F 2/95 604/523 |
| 7,465,288 B2 | 12/2008 | Dudney et al. | |
| 7,488,337 B2 | 2/2009 | Saab et al. | |
| 7,503,914 B2 | 3/2009 | Coleman et al. | |
| 7,780,716 B2* | 8/2010 | Pappas | A61F 2/95 623/1.11 |
| 8,062,345 B2 | 11/2011 | Ouellette et al. | |
| 8,523,933 B2* | 9/2013 | Nabulsi | A61F 2/95 623/1.11 |
| 8,579,963 B2* | 11/2013 | Tabor | A61F 2/2436 623/1.11 |
| 8,585,750 B2* | 11/2013 | Argentine | A61F 2/95 623/1.12 |
| 2003/0236493 A1 | 12/2003 | Mauch | |
| 2004/0127912 A1* | 7/2004 | Rabkin | A61F 2/95 606/108 |
| 2006/0142694 A1* | 6/2006 | Bednarek | A61M 25/0136 604/95.04 |
| 2007/0156224 A1* | 7/2007 | Cioanta | A61F 2/95 623/1.11 |
| 2010/0298832 A1 | 11/2010 | Lau et al. | |
| 2012/0221091 A1* | 8/2012 | Hartly | A61F 2/95 623/1.11 |
| 2013/0030520 A1* | 1/2013 | Lee | A61F 2/2433 623/2.11 |
| 2013/0345765 A1 | 12/2013 | Brockman et al. | |
| 2014/0276613 A1* | 9/2014 | Goodman | A61M 25/0147 604/510 |

OTHER PUBLICATIONS

BSC, "Blazer" (http://www.bostonscientific.com/templatedata/imports/collateral/Electrophysiology/crr_com/EPT-10874-01-BlazerPrimeBroc_DEC-2010.pdf).

Corevalve, "Delivery System" (http://www.medtronic.com/corevalve/ous/downloads/CoreValveProductBrochure.pdf).

IDev, "Supera Delivery System" (http://www.idevmd.com/deliverySystem.html).

Medtronic Captivia, "Delivery System" (http://www.medtronic.com/for-healthcare-professionals/products-therapies/cardiovascular/aortic-stent-grafts/talent-thoracic-on-captivia/index.htm).

St. Jude Agilis, "Steerable Introducer" (http://www.sjmprofessional.com/Products/US/EP-Access-Tools/Agilis-NxT-Steerable-Introducer.aspx).

* cited by examiner

UNIVERSAL CATHETER HANDLE

CROSS-REFERENCE TO RELATED APPLICATIONS

This application claims the benefit of the filing dates of the following U.S. Provisional patent applications: U.S. Ser. No. 61/901,650 filed Nov. 8, 2013; U.S. Ser. No. 61/763,111 filed Feb. 11, 2013; and U.S. Ser. No. 61/762,436 filed Feb. 8, 2013. The complete contents of these earlier Provisional applications are incorporated herein by reference.

FIELD OF INVENTION

This invention relates generally to a catheter actuation handle assembly for medical or surgical use. The catheter handle is specially designed and configured for convenient and easy manipulation of one or more distally-extending members to achieve translation, articulation and/or rotation of these distally-extending members by means of the catheter handle.

BACKGROUND OF THE INVENTION

Catheter apparatuses for a wide variety of medical and surgical applications are well known in the art. These catheter apparatuses commonly comprise a catheter handle at a proximal end of the catheter apparatus and one or more distally-extending members, which term is meant herein to include catheter tubes or shafts (defining one or a plurality of catheter lumens), guide wires, balloon members, actuation/control/pull wires and other types of catheter members that extend distally from the catheter handle, or from a given point within the catheter handle. The term distally-extending members specifically includes a plurality of distally-extending catheter shafts configured in annular or side-by-side relationship to one another, as well as articulation/control/pull wires used to actuate a function at the distal end of a catheter apparatus.

The catheter handle is intended to remain outside the body of a patient being treated and to serve as a base, a hand grip and a controller for a practitioner to manually or automatically manipulate the catheter apparatus and particularly the distally-extending members for treating the patient. In some applications, the catheter handle may also comprise one or more ports and related fluid tubes for introducing and/or removing fluids, for example to inflate/deflate a catheter balloon element, to flush an internal body location, to introduce drugs/medicines to an internal body site, to heat or cool parts of the apparatus and/or an internal body location, and other such applications.

Catheter members, such as catheter shafts and guide wires, extend distally from the catheter handle, and at least the distal portions of at least some of these catheter members are intended to extend internally into a patient's body during a medical or surgical treatment procedure. It is commonly desirable for a practitioner to manipulate portions of one or more of those distally-extending members from the catheter handle while the catheter apparatus is in use and while one or more of the distally-extending members is/are located at least in part inside the patient's body. Traditionally, catheter actuation handles are developed on an application-specific basis in which a particular handle design is utilized for a single set of end use conditions.

Catheter actuation handles are known in the art which are capable of realizing certain types of manipulation of distally-extending members. The prior art in this field includes the following patents, published patent applications, and technical and commercial publications: U.S. Pat. No. 7,488,337 (Apparatus and Methods for Bone, Tissue and Duct Dilatation); U.S. Pat. No. 7,503,914 (Dual-function Catheter Handle); U.S. Pat. Publ. No. US 2003/0236493 A1 (Articulating Handle for a Deflectable Catheter and Method Therefor); European Pat. No. EP1358903 B1 (Integrated Mechanical Handle with Quick Slide Mechanism); U.S. Pat. No. 6,171,277 (Bi-directional Control Handle for Steerable Catheter); U.S. Pat. No. 7,465,288 (Actuation Handle for a Catheter); U.S. Pat. No. 6,783,521 (Deflectable Catheter); U.S. Pat. No. 5,254,088 (Catheter Steering Mechanism); U.S. Pat. No. 5,391,172 (Stent Delivery System with Coaxial Catheter Handle); U.S. Pat. No. 8,062,345 (Delivery Systems for Delivering and Deploying Stent Grafts); U.S. Design Pat. No. D347,473 (Steerable Catheter Handle); European Pat. No. EP 1942975 A1 (Steerable Catheter Devices and Methods of Articulating Catheter Devices); European Pat. No. EP 1117341 A1 (Delivery Mechanism for Implantable Stent); St. Jude Agilis, "Steerable Introducer" (http://www.sjmprofessional.com/Products/US/EP-Access-Tools/Agilis-NxT-Steerable-Introducer.aspx); Medtronic Captivia, "Delivery System" (http://www.medtronic.com/for-healthcare-professionals/products-therapies/cardiovascular/aortic-stent-grafts/talent-thoracic-on-captivia/index.htm); Corevalve, "Delivery System" (http://www.medtronic.com/corevalve/ous/downloads/CoreValveProductBrochure.pdf); Bard, "Radia XT" (http://www.bardep.com/pdf/BAW04Z0650.pdf); BSC, "Blazer" (http://www.bostonscientific.com/templatedata/imports/collateral/Electrophysiology/crr_com/EP T-10874-01-BlazerPrimeBroc_DEC-2010.pdf); IDev, "Supera Delivery System" (http://www.idevmd.com/deliverySystem.html).

The complete disclosure of each of the above-listed patents, published patent applications and technical and commercial publications is incorporated herein by reference in their entireties.

These prior art approaches to catheter actuation handles, however, are deficient in one or more respects, such as being awkward to use, or being limited in their capability of achieving concurrent and, possibly, different types of manipulation of different catheter members, or requiring costly and time-consuming customized design, fabrication and assembly for a particular application. The prior art in this field does not teach a modular catheter actuation handle comprised of a standardized and, at least in part, interchangeable set of component parts, that can be configured or reconfigured relatively quickly to adapt the catheter handle to a particular combination of desired manipulation operations on the distally-extending members.

Furthermore, several types of manipulation of single or multiple distally-extending members may be desirable but not readily achievable with known catheter actuation handle technology, including such operations as: (1) "full-stroke" translation (axial movement) of one catheter shaft relative to one or more other catheter shafts or other catheter members; (2) articulation (bending) of a stationary outer catheter shaft with concurrent translation of an inner catheter shaft; (3) translation of an outer catheter shaft with concurrent articulation of a stationary inner catheter shaft; (4) independent translation, articulation or rotation of one catheter shaft relative to one or more other catheter shafts; and, (5) independent translation, articulation or rotation of two out of three or more catheter shafts relative to a third stationary catheter shaft.

The present invention enables one to realize types of manipulations of distally-extending members, including multiple manipulations and/or combinations of manipulations, that were realizable only with a specially designed, single-purpose catheter handle apparatus.

Objects of the Invention

Accordingly, a general object of this invention is to provide a catheter actuation handle embodiment designed and configured to actuate one or more distally-extending members to realize one or more of the operations of translation, articulation and/or rotation of these distally-extending members.

Another general object of this invention is to provide a catheter actuation handle embodiment comprised of a set of standardized and, at least in part, interchangeable component parts that can be configured or reconfigured relatively quickly to adapt the catheter handle to perform a desired combination of translation, articulation and rotation functionalities.

A further general object of this invention is to provide a catheter actuation handle embodiment comprised of an exterior shell, or for some embodiments, comprised of a plurality of axially aligned, connected but spatially separated exterior shell segments, that defines an exterior shell cavity where each exterior shell or exterior shell segment consists of mateable pairs of exterior shell halves, together with one or more moveable components positioned in the exterior shell cavity which correspond with and/or function in cooperation with geometrical features along inner and/or outer surfaces of the exterior shell halves in order to cause translation, articulation and/or rotation of connected distally-extending members.

Another general object of this invention is to provide a catheter actuation handle embodiment comprising at least an exterior shell that houses at least a moveable component (which, in alternative embodiments, may be a "driver", a cam member, a pivot assembly, a rotatable knob, or another type of moveable mechanical component whose movement can, in turn, impart or transfer that movement to a second, connected mechanical component) in combination with an actuation component that engages a moveable component, and an access port in the exterior shell through which the moveable component and/or the actuation component is accessed.

A more specific object of this invention is to provide a catheter actuation handle embodiment comprised of an exterior shell (or axially aligned exterior shell segments), consisting of a mateable pair of exterior shell halves, and an interior shell (or axially aligned interior shell segments), each consisting of a mateable pair of interior shell halves, that fits inside the exterior shell and houses at least a moveable component comprising a moveable "driver" (as hereinafter described) that corresponds with and/or functions in cooperation with geometrical features along inner and/or outer surfaces of the exterior and/or interior shell halves in order to cause, upon actuation, translation, articulation and/or rotation of distally-extending members.

Another more specific object of this invention is to provide a catheter actuation handle embodiment comprised of an exterior shell (or axially aligned exterior shell segments), consisting of a mateable pair of exterior shell halves, and an interior shell (or axially aligned interior shell segments), each consisting of a mateable pair of interior shell halves, that fits inside the exterior shell and houses at least a moveable component comprising a moveable "driver" (as hereinafter described) in combination with an actuation component that engages the driver, and an access port through the exterior shell through which an actuation component is actuated to move the engaged driver.

Another specific object of this invention is to provide a catheter actuation handle embodiment comprised of an exterior shell, an interior shell nested inside the exterior shell and accessible via an access port, and one or more substantially identically-sized, externally-threaded "drivers" that serve as the moveable components housed within the interior shell, where the threading of at least one of the drivers engages corresponding threading on an inner surface of the interior shell such that rotation of the interior shell via the access port causes movement of the threadably-engaged driver and, thereby, also movement of any distally-extending member connected to that driver.

Another specific object of this invention is to provide a catheter actuation handle embodiment with the functionality to provide full-stroke translation of one catheter shaft/distally-extending member relative to one or more other catheter shafts/distally-extending members.

Another specific object of this invention is to provide a catheter actuation handle embodiment with the functionality to provide articulation of a stationary outer catheter shaft/distally-extending member with concurrent translation of an inner catheter shaft/distally-extending member.

Another specific object of this invention is to provide a catheter actuation handle embodiment with the functionality to provide translation of an outer catheter shaft/outer distally-extending member with concurrent articulation of a stationary inner catheter shaft/inner distally-extending member.

Another specific object of this invention is to provide a catheter actuation handle embodiment with the functionality to provide independent translation, articulation or rotation of one catheter shaft/distally-extending member relative to one or more other catheter shafts/distally-extending members.

Another specific object of this invention is to provide a catheter actuation handle embodiment with the functionality to provide independent translation, articulation or rotation of two out of three or more catheter shafts/distally-extending members relative to a third stationary catheter shaft/distally-extending member.

Still another specific object of this invention is to provide a catheter actuation handle embodiment with the functionality to provide bilateral articulation of one or more catheter shafts or other distally-extending members.

Yet another specific object of this invention is to provide a catheter actuation handle embodiment with a segmented interior shell configuration such that there are two or more separate axially aligned interior shell segments (each comprising a pair of mateable interior shell halves), nested inside an exterior shell, such that the interior shell segments are capable of independent rotation about the longitudinal axis of the catheter handle.

Another specific object of this invention is to provide a catheter actuation handle embodiment with a segmented interior shell configuration such that there are two or more separate axially aligned interior shell segments (each comprising a pair of mateable interior shell halves), nested inside an exterior shell, such that the interior shell segments are capable of independent rotation about the longitudinal axis of the catheter handle, and further wherein at least two of the interior shell segments have threading along their inner surfaces that engages correspondingly threaded "drivers" positioned inside the interior shell segments to function as the moveable components.

Another specific object of this invention is to provide a catheter actuation handle embodiment with one or more access ports in an exterior shell through which communication from outside the exterior shell is established with an interior shell that threadably engages a driver, or with a plurality of such interior shell segments, or, alternatively, directly with a driver, for example by means of an outwardly-projecting knob feature of an interior shell.

Another specific object of this invention is to provide a catheter actuation handle embodiment having one or more fluid inlet ports and associated fluid lines through which fluid communication can be established from a location/locations outside the exterior shell to a fluid conduit/conduits running through the interior of the catheter handle so as to deliver flushing fluid, or another fluid, to locations in the exterior shell cavity and/or to the proximal ends of lumens of catheter shafts or other distally-extending members that originate in the exterior shell cavity.

Still another object of this invention is to provide a catheter actuation handle embodiment that includes one or more diaphragms, washers, guide rails and other such components positioned in the exterior shell cavity for providing sealing, support and rotation-resistance functions as hereinafter described.

Yet another object of this invention is to provide a set of standardized and, at least in part, interchangeable component parts from which a catheter actuation handle according to this invention can be assembled to meet a desired functionality according to a set of standardized steps, for example the general steps of: nesting a lower interior shell half segment inside a lower exterior shell half segment; positioning actuation handle interior components that is, the components housed inside the exterior shell cavity, including one or more substantially identical, externally-threaded drivers or other types of moveable components, in the open interior of the nested lower half shell; connecting proximal ends of one or more catheter shafts, guide wires, pull wires, or other distally-extending members, to one or more of the threadably-engaged drivers and/or to other handle interior components; mating the upper interior shell half segments with the lower interior shell half segments; mating the upper exterior shell half segments with the lower exterior shell half segments; and securing together the upper and lower exterior shell halves by screws, pins or another fastening mechanism to complete the catheter actuation handle assembly.

These and other objects of the invention will be apparent from the following description which is to be read together with the accompanying drawings.

SUMMARY OF THE INVENTION

Catheter actuation handles according to this invention facilitate controlled, convenient and adaptable manipulations of one or more distally-extending members using the catheter handle. The types of distally-extending members that can be controlled and manipulated using this invention include one or a plurality of catheter shafts (and their associated lumens), guide wires, pull wires, balloons (expandable) members, and other such catheter members. These catheter members typically extend from the distal end of the catheter handle and, during catheter use, are intended to be, at least in part, inside the body of a patient being treated. Therefore, when a catheter apparatus is in use, the only way to manipulate these distally-extending members is remotely from a location outside the patient's body, such as with the catheter handle.

The catheter actuation handles of this invention are generally of a cylindrical shape and consist of a set of component parts, sized and configured to fit together and, when assembled, to form a completed catheter actuation handle. The components of the catheter actuation handles of this invention may include: one or more pairs of mateable exterior shell halves (which can be symmetrical for some invention embodiments but not symmetrical for other embodiments) that together form a generally cylindrical exterior shell (which is also referred to herein as the "actuation handle housing"); one or more pairs of mateable interior shell halves (which can be symmetrical for some invention embodiments but not symmetrical for other embodiments) that together form a generally cylindrical interior shell; and various handle interior components (e.g., stationary and moveable drivers or other types of moveable components, actuation components, guide rails, seals and washers) that are sized and configured to engage with geometrical features in, on or along the side walls or the inner or outer surfaces of the exterior shell halves, the interior shell halves, or both to facilitate manipulation/articulation of distally-extending members. As described further below, the interior shell can, in some embodiments, comprise two or more interior shell segments, where each interior shell segment consists of a pair of mateable interior shell halves, and the several interior shell segments are axially aligned and positioned adjacent to one another or in close axial proximity to one another inside the exterior shell.

As described hereinafter, and as shown in the accompanying drawings, the geometrical features in, on or along the side walls or the inner or outer surfaces of the interior and exterior shells that can facilitate manipulation operations may include: threading along the inner surfaces of the interior shell halves that threadably mate with corresponding threading on the outer surface of a driver; one or more knob features along outer surfaces of the interior shell halves; one or more circumferential ribs or outward projections along outer surfaces of the interior shell halves; one or more knob pockets or half-circular knob tracks along inner surfaces of the exterior shell halves at locations where an access port is located in the exterior shell; one or more circumferential ribs or inward projections along inner surfaces of the exterior shell halves where, in some embodiments, such ribs define proximal end and/or intermediate and/or distal end driver pockets in the exterior shell that are sized to accommodate driver components.

The several catheter actuation handle components are designed to be assembled in a "clam shell" fashion by the generally sequential steps of: (a) first "building" a lower half of the assembly by nesting a lower interior shell half (or the lower shell halves of multiple interior shell segments) inside a lower exterior shell half whereby geometrical features along the outer surface of the lower interior shell half nest inside correspondingly sized and shaped geometrical features along the inner surface of the lower exterior shell half; (b) next positioning the various handle interior components of the apparatus including, for example, one or more drivers, in their appropriate locations along the open interior region of the nested lower interior and exterior half shells; (c) positioning the distally-extending members (e.g., catheter shafts, guide wires, pull wires, etc.) at the appropriate locations along the axis of the catheter handle; (d) connecting one or more of the distally-extending members to one or more of the handle interior components, e.g., to one of the drivers; and, (e) finally completing the assembly by mating the upper interior shell half (or upper shell halves of multiple interior shell segments) with the lower interior shell half (or lower shell halves of multiple interior shell segments), then mating the upper exterior shell half with the lower exterior shell half, and securing the two exterior shell halves together, for example with screws or pins that extend through aligned screw or pin holes along the periphery of the exterior shell halves which step typically also secures all of the other catheter handle components in place. For some embodiments, the interior shell halves may, after being mated, also be fastened to one another using screws or pins. To assist in the assembly procedure, the mating edges of the interior shell halves and the exterior shell halves may include a shell halves mating feature, such as a series of projections and matching holes, to assist in maintaining the mateable shell halves in mated relationship until they are fastened. Although the preceding description describes a typical catheter handle assembly sequence, for particular embodiments that sequence may be modified and one or more of the assembly steps may be performed in a different order, in whole or in part, or, depending on the embodiment, completely eliminated.

As used in this application, the term "moveable component" refers generally to a component of the catheter actuation handle assembly that, in a fully assembled actuation handle, is positioned inside the exterior shell cavity, is connected directly or by means of one or more control wires to a distally-extending member, and is actuatable by engagement with an actuation component (as hereinafter defined) of the assembly for enabling controlled linear, rotational and/or pivoting movement of the moveable component.

In different invention embodiments, the movement of a moveable component can be linear translation of the moveable component along the longitudinal axis of the actuation handle, rotation of the moveable component about the longitudinal axis of the actuation handle, rotation of the moveable component about an axis at an angle (e.g., orthogonal) relative to the longitudinal axis of the actuation handle, pivoting of the moveable component about a point that is located inside the exterior shell cavity (e.g., along the longitudinal axis of the actuation handle), or some combination of such movements. Depending on the type of moveable component, the type of connection between a moveable component and a distally-extending member, and other structural/design features of the assembly (as hereinafter described), actuation of a moveable component can effect translation, rotation and/or articulation of a connected distally-extending member.

A variety of different types of components can be used as "moveable components" in accordance with this invention. One such component is referred herein as a "driver". As used in this application, the term "driver" refers to a generally cylindrical mechanical element having a driver axis and a driver diameter that is slightly smaller than the diameter of the shell cavity formed by mating pairs of interior and exterior shell halves. as elsewhere described. The length of a driver may be approximately the same as its diameter, although longer or shorter drivers may be used. A driver is positioned inside a mated pair of exterior and/or interior shell halves such that the driver axis aligns with the longitudinal axis of the mated shell halves.

In an embodiment, a driver is threaded along a circumferential outer surface with threads that can mate with corresponding threading along an inner surface of the interior shell halves. In an embodiment, a driver also includes a plurality of slots that run parallel to the driver axis and intersect the circumferential threading to accommodate the positioning of guide rails in the slots, as hereinafter described. In an embodiment, a driver also has a cylindrical driver protrusion from a driver protrusion end face, the protrusion diameter being smaller than the diameter of the threaded driver portion. In an embodiment, the driver protrusion includes a plurality of control wire slots that run parallel to the driver axis to accommodate the positioning of control wires in the slots as hereinafter described. In an embodiment, the driver end face that is opposite from the driver protrusion end face may include a driver end face recess for accommodating sealing and locking members.

Drivers in accordance with this invention may be moveable drivers or stationary drivers, and they may be positioned inside the actuation handle with the driver protrusion on either the proximal or distal end of the driver, depending on the intended function of the driver. A stationary driver may be substantially identical in size and shape to a moveable driver, but it may be positioned in a portion of the actuation handle (e.g., proximal or distal of the threaded interior shell) where it is not actuated for movement, or it may be secured in place (e.g., by pinning) to prevent driver movement. As described hereinafter, stationary drivers can function in cooperation with moveable drivers to effect certain desired types of manipulation of distally-extending members and/or to provide other types of functionality.

In other embodiments, instead of a moveable driver the "moveable component" of this invention may comprise a cam member, a pivot assembly, a rotatable knob, or another type of moveable mechanical component, in combination with suitable connections to distally-extending members and adapted for appropriate engagement with an actuation component.

As used in this application, the term "actuation component" refers generally to a component of the catheter actuation handle assembly that, in a fully assembled actuation handle, engages or can be made to engage a moveable component of the assembly and that is accessible from outside the actuation handle housing for manual manipulation. In alternative invention embodiments, an actuation component may be manipulated for linear translation along a track, for rotation about the longitudinal axis of the actuation handle, for rotation about an axis that is orthogonal relative to the longitudinal axis of the actuation handle, for pivoting about a point that is inside the exterior shell cavity, and/or for some combination of such movements.

In some embodiments, an actuation component completely or primarily located inside the exterior shell cavity is accessed for manipulation via an access port through the exterior shell/actuation handle housing, or a portion of the actuation component projects into or partially through the access port. In other embodiments, at least one portion of an actuation component is located completely outside the exterior shell/actuation handle housing and connects through an access port to a second portion of the actuation component or directly to the moveable component. In certain of these embodiments, the actuation component as defined herein may be a part of the moveable component.

In an embodiment, the linear motion required for either (a) relative translation of catheter shafts (translation/unsheathing) or other distally-extending members, or (b) actuation of a control/pull wire or other distally-extending members to induce shaft/member articulation, is effected using a segmentable lead-screw-based drive train configuration. Such a lead screw configuration may comprise a pair of internally threaded interior shell halves that combine to form a complete interior shell together with at least an externally threaded driver component that acts as a translating member in the interior region of the catheter handle by threadably engaging corresponding threading along the inside surface of the interior shell. Guide rails may also be positioned to run a portion of or the entire length of the interior region of the catheter handle. Such guide rails can engage guide rail slots in the threaded driver component(s) to selectively prevent their rotation relative to the catheter handle housing. The anti-rotation resistance provided by the guide rail/slotted driver configuration converts rotation of the interior shell into linear translation of the threadably-engaged driver and any distally-extending catheter members connected to the driver.

To increase the number of potential end-use permutations of the actuation apparatus in manipulating distally-extending members, the lead screw housing (i.e., the threaded interior shell) can be segmented to create distinct sections along the length of the catheter handle that are capable of being rotated independently of one another. In this way, the actuation handle of this invention can accommodate a variety of desirable catheter shaft/distally-extending member functionalities including, but not limited to, the following: full-stroke translation of one shaft/distally-extending member relative to one or a plurality of other stationary shafts/distally-extending members; articulation of a stationary outer shaft/distally-extending member with concurrent translation of an inner shaft/distally-extending member; translation of an outer shaft/distally-extending member with concurrent articulation of a stationary inner shaft/distally-extending member; independent translation or articulation of two out of three shafts/distally-extending members relative to a third stationary shaft/distally-extending member; and, any of the preceding manipulation operations in conjunction with rotation, for example a sequence of manipulations consisting of translation, articulation and rotation in any desirable order. Although the preceding examples of manipulation operations achievable with the present invention commonly refer to manipulations of catheter shafts, the same or similar functionality can be realized with this invention for various other types of distally-extending members or combinations of such catheter members.

A common feature of catheter handles generally is the need to provide means for sealing against leaks/openings and for flushing between catheter shafts at any shaft termination/transition points. Embodiments of this invention achieve these sealing and/or flushing features also in a modular fashion, i.e., using a universal seal design that can be modified to the required size so as to fit a given catheter shaft having a particular lumen size at a given location in the exterior shell cavity. A preferred seal design of an embodiment of this invention utilizes a compliant diaphragm that is compressively captured between compression elements that are attached to a threaded driver component of this invention or compressed between a compression element and the driver itself, for example, in a suitably sized and shaped recess or pocket that is formed in an end face of the driver. The internal diameter of the compliant diaphragm can easily be punched to size in order to effectively seal against an open end of a catheter shaft, for example catheter shafts in about the 5-24 F size range. The actuation handles of this invention, and the various components that comprise those handles, can be scaled up in size to accommodate larger catheter shafts or scaled down in size to accommodate smaller catheter shafts. Additionally, a centrally-located through-hole of the compressive/support sealing component could be initially fabricated at a maximum material condition (i.e., a minimum through-hole size) and subsequently be drilled out to a larger size such that it appropriately supports and aligns with an associated compliant diaphragm, thereby preventing seal incontinence when the system is pressurized for use.

Catheter actuation handles in accordance with this invention have the following advantageous features and utilities (among others): linear translation (sheathing/unsheathing) capability for a variety of catheter shaft/distally-extending member configurations, including full-stroke shaft translation capability; actuation of a control/pull wire (which may be capable of either a pulling or a pushing function) for single-side (one-directional) articulation of a catheter shaft/distally-extending member for a variety of shaft/distally-extending member configurations; manual rotation of a catheter shaft/distally-extending member which is accommodated by the symmetry of the catheter handle (for example, some elements could be actively rotated by coupling them directly to the interior shell); seal and flush capability at any/all catheter shaft transitions; and, compatibility with a wide range of catheter shaft sizes (e.g., 5-24 F). As noted above, the actuation handles of this invention can be scaled up or scaled down in size to accommodate different catheter shaft sizes.

Catheter actuation handles in accordance with this invention can also be configured for utilization in the various advantageous embodiments (among others) namely, (a) bilateral articulation and (b) actuation of multiple control/pull wires via a pivot assembly or swash-plate type of actuation component, for example:

(a) Bilateral Articulation:

An earlier described embodiment allows for unilateral articulation (i.e., in one direction such as by actuation of a single control/pull wire). For some applications, however, it is desirable to achieve bilateral articulation such that a catheter shaft/distally-extending member could be manipulated so as to flex its tip in two different directions, e.g., +180 degrees (or more, or less) as well as −180 degrees (or more, or less). Such bilateral articulation capability can be achieved with the present invention utilizing at least one of the embodiments described below.

One way of achieving such bilateral articulation with this invention is to use one or more rotatable heads as combination moveable components/actuation components. These rotatable heads are accessible through at least an access port in the exterior shell of the actuation handle. These rotatable heads can be rotationally actuated such that clockwise rotation of the head achieves catheter shaft articulation in one direction, while counterclockwise rotation achieves catheter shaft articulation in a different (e.g., opposite) direction. In this embodiment, the rotatable heads can each be fabricated as two head half-portions of the head geometry along and as a part of the outer surface of each of the interior shell halves. Such a rotatable head half-portion of the interior shell half could have an outside diameter equal to or, preferably, slightly greater than the outside diameter of the other portion of the interior shell half at the access port location. With this configuration, when the interior shell halves are mated, two rotatable head half-portions would then form a complete, cylindrically-shaped rotatable head accessible through the access port.

A half-circular rotatable head track or a rotatable head pocket that is sized to correspond to the size/shape of the rotatable head can be formed as one of the geometrical features along an exterior shell half at the location of each access port in the exterior shell half. In this way, when the actuation handle is fully assembled, the cylindrically-shaped rotatable head portion formed on the outer surface of the interior shell can rotate inside the correspondingly sized pocket or circular track of the exterior shell. The outer surface of each rotatable head portion may have geometrical features, such as grooves or indentations, that would facilitate manual rotation, for example using a thumb and forefinger.

The desired functionality with this configuration could be achieved, for example, by directing two control/pull wires such that they are anchored to a rotatable head at different selected points along the geometry of the rotatable head. The anchoring location of each control/pull wire would be chosen such that rotation of the rotatable head causes that wire to travel through an arc length during actuation that applies tension to the wire such that it is partially withdrawn into the exterior shell cavity sufficiently to achieve the desired degree of articulation of the tip of the associated distally-extending member.

Alternatively, another way of achieving bilateral articulation is to use a rotatable head portion sized so that it extends through the access port to provide an exposed portion that is above the surface of the exterior shell so that it can be positively or negatively rotated to achieve paired actuation of two control/pull wires that are anchored against a swiveling member positioned inside the exterior shell cavity.

In yet another alternative embodiment, one of the articulation control/pull wires required for bilateral articulation may be looped inside the exterior shell cavity and attached to the same translating driver such that actuation of the driver actively tensions one wire while simultaneously recovering slack on the opposing wire as it travels through its stroke, thereby achieving bilateral (+180° to −180°, more or less) articulation.

(b) Actuation of Two, Three, Four or More Control/Pull Wires Via a Swash-Plate Mechanism Incorporated into the Handle:

This approach can be utilized to achieve multi-axis articulation of a catheter shaft/distally-extending member. In its basic construction, this design includes a swash-plate type of mechanism as the moveable component which is capable of anchoring a plurality of control/pull wires to itself. This assembly design includes an anchor point that defines the pivot of the swash-plate, and a user interface (such as an arm, knob, or joystick) as the actuation component projecting from the actuation handle housing in such a way that it can be actuated by the user.

For some embodiments, a "rapid throw" version of the catheter actuation handle may be required to obtain the desired functional results. This functionality can be achieved, for example, with a spring-loaded puncture mechanism that includes a compressed spring and a spring-release element. This could be achieved by replacing one of the handle interior components (e.g., the lead screw portion) with a spring-loaded, or otherwise energized, shaft interface.

For certain applications, manual translation in which the user directly displaces a positioning button that is interfaced with a shaft/distally-extending member (such that axial movement of the positioning button directly translates to axial movement of the shaft, either by rigid attachment, spring-dampened junction, or other such means) may be desired. This embodiment of the actuation handle can be realized by providing a positioning button that slidably rides in an access port comprising an elongated slot longitudinally along the actuation handle housing (i.e., the exterior shell). An externally-projecting upper side of the positioning button can be actuated by a user such that a lower side of the button that is inside the exterior shell engages a distally-extending member at a location inside the actuation handle. A user can thereby manually translate the positioning button (and therefore the distally-extending member) back and forth along the length of the actuation handle within the confines of the elongated slot.

The following are some particular embodiments of this invention:

1. A catheter actuation handle assembly adapted to manipulate one or more distally-extending members that connect to the catheter handle and extend from the handle to locations distal from the handle for realizing translation, articulation and/or rotation of these distally-extending members using a combination of components comprising at least a moveable component that is connected to a distally-extending member and is actuated by an associated actuation component that can be manually manipulated, said handle assembly comprising:

at least a pair of mating exterior shell halves, each exterior shell half having an exterior shell outer surface and an exterior shell inner surface, the pair of exterior shell halves being mateable with one another to form a generally cylindrically-shaped actuation handle housing having a circular or ovular cross-section that defines an exterior shell cavity and a handle longitudinal axis;

at least a moveable component positioned inside the exterior shell cavity whereby the moveable component is enabled for controlled linear movement along, and/or rotational movement about, the longitudinal axis, or alternatively is enabled for controlled rotation about an axis orthogonal to the longitudinal axis, by means of engagement with one or more actuation components of the assembly;

at least a connection between the moveable component and a distally-extending member; and, one or more access ports through the actuation handle housing providing access into the exterior shell cavity for manipulating the moveable component and/or the actuating component from outside the actuation handle housing; the handle assembly being further characterized by one or more of the following features:

(a) an actuation component comprising a pair of mating interior shell halves forming a cylindrically-shaped interior shell segment that is sized to fit inside and rotate within the exterior shell cavity such that threading along an interior shell inner surface engages corresponding threading along an outer surface of a moveable component comprising a driver whereby rotation of the interior shell segment via an associated access port causes linear movement of the driver along the handle longitudinal axis;

(b) an actuation component comprising a pair of mating interior shell halves forming a cylindrically-shaped interior shell segment that is sized to fit inside and rotate within the exterior shell cavity such that threading along an interior shell inner surface engages corresponding threading along an outer surface of a moveable component comprising a driver whereby rotation of the interior shell segment via an associated access port causes linear movement of the driver along the handle longitudinal axis, and the assembly further comprises at least a stationary driver of substantially the same size and shape as the moveable driver but positioned inside the exterior shell cavity proximal or distal of the interior shell segment containing the moveable driver, and a connection between the stationary driver and a distally-extending member;

(c) an actuation component comprising a pair of mating interior shell halves forming a cylindrically-shaped interior shell segment that is sized to fit inside and rotate within the exterior shell cavity such that threading along an interior shell inner surface engages corresponding threading along an outer surface of a moveable component comprising a driver whereby rotation of the interior shell segment via an associated access port causes linear movement of the driver along the handle longitudinal axis, and the assembly further comprises at least first and second stationary drivers of substantially the same size and shape as the moveable driver but positioned inside the exterior shell cavity, one located proximal of and the other being distal of the interior shell segment containing the moveable driver;

(d) an actuation component comprising a pair of mating interior shell halves forming a cylindrically-shaped interior shell segment that is sized to fit inside and rotate within the exterior shell cavity such that threading along an interior shell inner surface engages corresponding threading along an outer surface of a moveable component comprising a driver whereby rotation of the interior shell segment via an associated access port causes linear movement of the driver along the handle longitudinal axis, and the assembly further comprises at least first and second stationary drivers of substantially the same size and shape as the moveable driver but positioned inside the exterior shell cavity, one located proximal of and the other being distal of the interior shell segment containing the moveable driver, and also including at least a pair of guide rails positioned in guide rail slots at different circumferential locations, such as on opposite sides, of the proximal stationary driver, and extending through corresponding guide rail slots of the moveable driver and to corresponding guide rail slots of the distal stationary driver to constrain rotation of the moveable driver during rotation of the interior shell segment;

(e) an actuation component comprising a pair of mating interior shell halves forming a cylindrically-shaped interior shell segment that is sized to fit inside and rotate within the exterior shell cavity such that threading along an interior shell inner surface engages corresponding threading along an outer surface of a moveable component comprising a driver whereby rotation of the interior shell segment via an associated access port causes linear movement of the driver along the handle longitudinal axis, and the assembly further comprises corresponding circumferential rib projections along the inner surfaces of the exterior shell halves and also along the outer surfaces of the interior shell halves to facilitate positioning and rotation of the interior shell inside the exterior shell cavity;

(f) an actuation component comprising a pair of mating interior shell halves forming a cylindrically-shaped interior shell segment that is sized to fit inside and rotate within the exterior shell cavity such that threading along an interior shell inner surface engages corresponding threading along an outer surface of a moveable component comprising a driver whereby rotation of the interior shell segment via an associated access port causes linear movement of the driver along the handle longitudinal axis, and the assembly further comprises at least first and second stationary drivers of substantially the same size and shape as the moveable driver but positioned inside the exterior shell cavity, one located proximal of and the other being distal of the interior shell segment containing the moveable driver, and the assembly also comprises circumferential rib projections along the inner surfaces of the exterior shell halves at their proximal and distal ends that define pockets for accommodating, respectively, the proximal end and distal end stationary drivers;

(g) an actuation component comprising a pair of mating interior shell halves forming a cylindrically-shaped interior shell segment that is sized to fit inside and rotate within the exterior shell cavity such that threading along an interior shell inner surface engages corresponding threading along an outer surface of a moveable component comprising a driver whereby rotation of the interior shell segment via an associated access port causes linear movement of the driver along the handle longitudinal axis, and the moveable driver comprises a threaded driver end having a first diameter with circumferential threading along the outer surface and axially-oriented guide rail slots intersecting the threading, and an unthreaded protrusion driver end having a second diameter, smaller than the first diameter, and with axially-oriented control wire slots along the outer surface;

(h) an actuation component comprising a pair of mating interior shell halves forming a cylindrically-shaped interior shell segment that is sized to fit inside and rotate within the exterior shell cavity such that threading along an interior shell inner surface engages corresponding threading along an outer surface of a moveable component comprising a driver whereby rotation of the interior shell segment via an associated access port causes linear movement of the driver along the handle longitudinal axis, and the moveable driver comprises a threaded driver end having a first diameter with circumferential threading along the outer surface and axially-oriented guide rail slots intersecting the threading, and an unthreaded protrusion driver end having a second diameter, smaller than the first diameter, and with axially-oriented control wire slots along the outer surface, and further wherein the threaded driver end includes an end face with a recess sized and shaped to receive sealing and locking elements;

(i) at least two moveable components comprising drivers of substantially the same size and shape, each associated with a driver-distal member control wire that connects the moveable driver to a distally-extending member;

(j) at least two moveable components comprising drivers of substantially the same size and shape, each associated with a driver-distal member control wire that connects the moveable driver to a distally-extending member, and further where each of the moveable drivers is located in a separate, independently rotatable interior shell segment such that it can be actuated independently of the other moveable drivers;

(k) at least two moveable components comprising drivers of substantially the same size and shape, each associated with a driver-distal member control wire that connects the moveable driver to a distally-extending member, and also an actuation component associated with each moveable driver, each actuation component comprising a pair of mating interior shell halves forming a cylindrically-shaped interior shell segment that is sized to fit inside and rotate within the exterior shell cavity such that threading along an interior shell inner surface engages corresponding threading along an outer surface of the driver whereby rotation of the interior shell segment via an associated access port causes linear movement of the driver along the handle longitudinal axis;

(l) at least two moveable components comprising drivers of substantially the same size and shape, each associated with a driver-distal member control wire that connects the moveable driver to a distally-extending member, and also an actuation component that comprises a pair of mating interior shell halves forming a cylindrically-shaped interior shell segment that is sized to fit inside and rotate within the exterior shell cavity such that first threading along a first portion of the interior shell inner surface engages corresponding threading along an outer surface of a first moveable driver, and second threading of a different orientation direction and/or a different pitch than the first threading along a second portion of the interior shell inner surface engages corresponding threading along an outer surface of a second moveable driver, whereby rotation of the interior shell segment housing the first and second moveable drivers via an associated access port results in linear movement of both moveable drivers but in different directions or at different rates of movement;

(m) a shell half connection system selected from a plurality of corresponding threaded exterior shell screw holes that are located along the periphery of the exterior shell halves and a set of screws sized and threaded to match the exterior shell screw holes or a snap-fit connection system is used to fasten the exterior shell halves together;

(n) an actuation component comprising a pair of mating interior shell halves forming a cylindrically-shaped interior shell segment that is sized to fit inside and rotate within the exterior shell cavity such that threading along an interior shell inner surface engages corresponding threading along an outer surface of a moveable component comprising a driver whereby rotation of the interior shell segment via an associated access port causes linear movement of the driver along the handle longitudinal axis, and also a shell half connection system selected from a plurality of corresponding threaded interior shell screw holes that are located along the periphery of the interior shell halves and a set of screws sized and threaded to match the interior shell screw holes or a snap-fit connection system is used to fasten the interior shell halves together;

(o) an actuation component comprising a pair of mating interior shell halves forming a cylindrically-shaped interior shell segment that is sized to fit inside and rotate within the exterior shell cavity such that threading along an interior shell inner surface engages corresponding threading along an outer surface of a moveable component comprising a driver whereby rotation of the interior shell segment via an associated access port causes linear movement of the driver along the handle longitudinal axis, and also one or more knob features along the outer surface of the interior shell at locations where the knob features align with and project at least partly into or through an access port;

(p) at least two moveable components comprising drivers of substantially the same size and shape, each associated with a driver-distal member control wire that connects the moveable driver to a distally-extending member, and further where each of the moveable drivers is located in a separate, independently rotatable interior shell segment such that it can be actuated independently of the other moveable drivers, and also a knob feature along the outer surface of each interior shell segment that houses a moveable driver where the knob feature aligns with and projects at least partly into or through an access port;

(q) at least two moveable components comprising drivers of substantially the same size and shape, each associated with a driver-distal member control wire that connects the moveable driver to a distally-extending member, and further where each of the moveable drivers is located in a separate, independently rotatable interior shell segment such that it can be actuated independently of the other moveable drivers, and also a slotted support washer positioned between at least two of the separate interior shell segments with slots sized and located to accommodate a pair of guide rails that extend between the most proximal and the most distal drivers;

(r) at least two moveable components comprising drivers of substantially the same size and shape, each associated with a driver-distal member control wire that connects the moveable driver to a distally-extending member, and further where each of the moveable drivers is located in a separate, independently rotatable interior shell segment such that it can be actuated independently of the other moveable drivers, and also a distal-end stationary driver positioned distal of the most distal of the moveable drivers, a proximal-end stationary driver positioned proximal of the most proximal of the moveable drivers, and a mid-body stationary driver positioned between the most distal moveable driver and the most proximal moveable driver;

(s) at least two moveable components comprising drivers of substantially the same size and shape, each associated with a driver-distal member control wire that connects the moveable driver to a distally-extending member, and further where each of the moveable drivers is located in a separate, independently rotatable interior shell segment such that it can be actuated independently of the other moveable drivers, and also a distal-end stationary driver positioned distal of the most distal of the moveable drivers, a proximal-end stationary driver positioned proximal of the most proximal of the moveable drivers, and a mid-body stationary driver positioned between the most distal moveable driver and the most proximal moveable driver, and also slotted support washers positioned between the interior shell segment housing the mid-body stationary driver and the distal and proximal interior shell segments housing, respectively, the distal moveable driver and the proximal moveable driver, each slotted support washer having slots sized and located to accommodate a pair of guide rails that extend between the most proximal and the most distal drivers;

(t) a moveable driver-distal member control wire that connects at least one moveable driver to a distally-extending member;

(u) at least one stationary driver located within the exterior shell cavity together with a stationary driver-distal member control wire that connects at least one of the stationary drivers to a distally-extending member;

(v) at least one stationary driver located within the exterior shell cavity together with a stationary driver-distal member control wire that connects at least one of the stationary drivers to a distally-extending member, and also a moveable driver-distal member control wire that connects at least one moveable driver to a distally-extending member;

(w) a moveable driver-distal member control wire that connects at least one moveable driver to a distally-extending member, and at least one stationary driver connected to a distally-extending member;

(x) a moveable driver-distal member control wire that connects at least one moveable driver to a distally-extending member, and a guide sleeve that houses at least a portion of the moveable driver-distal member control wire that is in the exterior shell cavity;

(y) an actuation component comprising a pair of mating interior shell halves forming a cylindrically-shaped interior shell segment that is sized to fit inside and rotate within the exterior shell cavity such that threading along an interior shell inner surface engages corresponding threading along an outer surface of a moveable component comprising a driver whereby rotation of the interior shell segment via an associated access port causes linear movement of the driver along the handle longitudinal axis, and the moveable driver comprises a threaded driver end having a first diameter with circumferential threading along the outer surface and axially-oriented guide rail slots intersecting the threading, and an unthreaded protrusion driver end having a second diameter, smaller than the first diameter, and with axially-oriented control wire slots along the outer surface, and a moveable driver-distal member control wire that passes through one of the driver's control wire slots in connecting the moveable driver to a distally-extending member;

(z) a fluid line that extends from outside the actuation handle housing into the interior shell cavity, where it connects to a driver and/or to a distally-extending member and/or to another fluid tube that connects to a driver and/or a distally-extending member;

(aa) an actuation component that comprises a pair of mating interior shell halves forming a cylindrically-shaped interior shell segment that is sized to fit inside and rotate within the exterior shell cavity and a moveable component comprising a driver housed inside and attached to the interior shell segment whereby rotation of the interior shell segment via an associated access port results in rotation of the moveable driver and the distally-extending members connected to the driver;

(bb) a moveable component comprising a rotatable cam member pivoted inside the exterior shell cavity to rotate about an axis that is orthogonal to the handle longitudinal axis; a pair of opposing cam-distal member control wires that connect different portions of the cam member to a distally-extending member; and, a knob feature connected to the cam member and projecting through an access port that aligns with the cam member;

(cc) a moveable component comprising a moveable driver located within the exterior shell cavity; a pair of driver-distal member control wires providing two connections between the driver and a distally-extending member, where a first of the control wires connects directly to a connection point of the driver, while a second of the control wires is routed through the exterior shell cavity to a location proximal of the driver where it loops around and returns to the driver connection point; and, an actuation component for translating the driver distally or proximally along the axis of the actuation handle;

(dd) a moveable component comprising a rotational knob adapted to rotate about the axis of the actuation handle at an axial location where it aligns with an access port; a pair of knob-distal member control wires providing two connections between the rotational knob and a distally-extending member; and, an actuation component comprising a geometrical feature along the circumference of the rotational knob that facilitates rotation of the knob via the access port;

(ee) a moveable component comprising a pivot assembly adapted to pivot about a point along the axis of the actuation handle at an axial location where it aligns with an access port; two or more pivot-distal member control wires providing multiple connections between the pivot assembly and a distally-extending member; and, an actuation component comprising a plate member exterior of the actuation handle housing that is connected to the pivot assembly via the access port;

(ff) a spring-loaded component comprising a compressed spring element located within the exterior shell cavity and connected to a distally-extending member such that release of the compressed spring element via an access port drives the distally-extending member rapidly and forcefully in the distal direction, in combination with a spring-release mechanism;

(gg) an actuation component comprising a positioning button having upper and lower sides that slidably rides in an access port comprising an elongated slot in the actuation handle housing that parallels the handle longitudinal axis, also where the upper side of the positioning button is exterior to the actuation handle housing while the lower side is within the exterior shell cavity, and the lower side has a geometrical feature that can releasably engage the moveable driver for linear movement along the longitudinal axis; and/or, (hh) an actuation handle housing comprising two pairs of mating exterior shell halves, one of which is a distal exterior shell segment and the other a proximal exterior shell segment that houses the moveable component, where the distal segment and the proximal segment are axially spatially separated but connected such that the distal segment can be articulated relative to the longitudinal axis of the proximal segment, and also where the spatial separation constitutes the access port.

2. A catheter actuation handle assembly according to paragraph 1 above wherein the handle assembly is characterized by an actuation component comprising a pair of mating interior shell halves forming a cylindrically-shaped interior shell segment that is sized to fit inside and rotate within the exterior shell cavity such that threading along an interior shell inner surface engages corresponding threading along an outer surface of a moveable component comprising a driver whereby rotation of the interior shell segment via an associated access port causes linear movement of the driver along the handle longitudinal axis.

3. A catheter actuation handle assembly according to any of paragraphs 1-2 above wherein the handle assembly is characterized by an actuation component comprising a pair of mating interior shell halves forming a cylindrically-shaped interior shell segment that is sized to fit inside and rotate within the exterior shell cavity such that threading along an interior shell inner surface engages corresponding threading along an outer surface of a moveable component comprising a driver whereby rotation of the interior shell segment via an associated access port causes linear movement of the driver along the handle longitudinal axis, and the assembly further comprises at least a stationary driver of substantially the same size and shape as the moveable driver but positioned inside the exterior shell cavity proximal or distal of the interior shell segment containing the moveable driver, and a connection between the stationary driver and a distally-extending member.

4. A catheter actuation handle assembly according to any of paragraphs 1-3 above wherein the handle assembly is characterized by an actuation component comprising a pair of mating interior shell halves forming a cylindrically-shaped interior shell segment that is sized to fit inside and rotate within the exterior shell cavity such that threading along an interior shell inner surface engages corresponding threading along an outer surface of a moveable component comprising a driver whereby rotation of the interior shell segment via an associated access port causes linear movement of the driver along the handle longitudinal axis, and the assembly further comprises at least first and second stationary drivers of substantially the same size and shape as the moveable driver but positioned inside the exterior shell cavity, one located proximal of and the other being distal of the interior shell segment containing the moveable driver.

5. A catheter actuation handle assembly according to any of paragraphs 1-4 above wherein the handle assembly is characterized by an actuation component comprising a pair of mating interior shell halves forming a cylindrically-shaped interior shell segment that is sized to fit inside and rotate within the exterior shell cavity such that threading along an interior shell inner surface engages corresponding threading along an outer surface of a moveable component comprising a driver whereby rotation of the interior shell segment via an associated access port causes linear movement of the driver along the handle longitudinal axis, and the assembly further comprises at least first and second stationary drivers of substantially the same size and shape as the moveable driver but positioned inside the exterior shell cavity, one located proximal of and the other being distal of the interior shell segment containing the moveable driver, and also including at least a pair of guide rails positioned in guide rail slots on opposite sides of the proximal stationary driver, and extending through corresponding guide rail slots of the moveable driver and to corresponding guide rail slots of the distal stationary driver to constrain rotation of the moveable driver during rotation of the interior shell segment.

6. A catheter actuation handle assembly according to any of paragraphs 1-5 above wherein the handle assembly is characterized by an actuation component comprising a pair of mating interior shell halves forming a cylindrically-shaped interior shell segment that is sized to fit inside and rotate within the exterior shell cavity such that threading along an interior shell inner surface engages corresponding threading along an outer surface of a moveable component comprising a driver whereby rotation of the interior shell segment via an associated access port causes linear movement of the driver along the handle longitudinal axis, and the assembly further comprises corresponding circumferential rib projections along the inner surfaces of the exterior shell halves and also along the outer surfaces of the interior shell halves to facilitate positioning and rotation of the interior shell inside the exterior shell cavity.

7. A catheter actuation handle assembly according to any of paragraphs 1-6 above wherein the handle assembly is characterized by an actuation component comprising a pair of mating interior shell halves forming a cylindrically-shaped interior shell segment that is sized to fit inside and rotate within the exterior shell cavity such that threading along an interior shell inner surface engages corresponding threading along an outer surface of a moveable component comprising a driver whereby rotation of the interior shell segment via an associated access port causes linear movement of the driver along the handle longitudinal axis, and the assembly further comprises at least first and second stationary drivers of substantially the same size and shape as the moveable driver but positioned inside the exterior shell cavity, one located proximal of and the other being distal of the interior shell segment containing the moveable driver, and the assembly also comprises circumferential rib projections along the inner surfaces of the exterior shell halves at their proximal and distal ends that define pockets for accommodating, respectively, the proximal end and distal end stationary drivers.

8. A catheter actuation handle assembly according to any of paragraphs 1-7 above wherein the handle assembly is characterized by an actuation component comprising a pair of mating interior shell halves forming a cylindrically-shaped interior shell segment that is sized to fit inside and rotate within the exterior shell cavity such that threading along an interior shell inner surface engages corresponding threading along an outer surface of a moveable component comprising a driver whereby rotation of the interior shell segment via an associated access port causes linear movement of the driver along the handle longitudinal axis, and the moveable driver comprises a threaded driver end having a first diameter with circumferential threading along the outer surface and axially-oriented guide rail slots intersecting the threading, and an unthreaded protrusion driver end having a second diameter, smaller than the first diameter, and with axially-oriented control wire slots along the outer surface.

9. A catheter actuation handle assembly according to any of paragraphs 1-8 above wherein the handle assembly is characterized by an actuation component comprising a pair of mating interior shell halves forming a cylindrically-shaped interior shell segment that is sized to fit inside and rotate within the exterior shell cavity such that threading along an interior shell inner surface engages corresponding threading along an outer surface of a moveable component comprising a driver whereby rotation of the interior shell segment via an associated access port causes linear movement of the driver along the handle longitudinal axis, and the moveable driver comprises a threaded driver end having a first diameter with circumferential threading along the outer surface and axially-oriented guide rail slots intersecting the threading, and an unthreaded protrusion driver end having a second diameter, smaller than the first diameter, and with axially-oriented control wire slots along the outer surface, and further wherein the threaded driver end includes an end face with a recess sized and shaped to receive sealing and locking elements.

10. A catheter actuation handle assembly according to any of paragraphs 1-9 above wherein the handle assembly is characterized by at least two moveable components comprising drivers of substantially the same size and shape, each associated with a driver-distal member control wire that connects the moveable driver to a distally-extending member.

11. A catheter actuation handle assembly according to any of paragraphs 1-10 above wherein the handle assembly is characterized by at least two moveable components comprising drivers of substantially the same size and shape, each associated with a driver-distal member control wire that connects the moveable driver to a distally-extending member, and further where each of the moveable drivers is located in a separate, independently rotatable interior shell segment such that it can be actuated independently of the other moveable drivers.

12. A catheter actuation handle assembly according to any of paragraphs 1-11 above wherein the handle assembly is characterized by at least two moveable components comprising drivers of substantially the same size and shape, each associated with a driver-distal member control wire that connects the moveable driver to a distally-extending member, and also an actuation component associated with each moveable driver, each actuation component comprising a pair of mating interior shell halves forming a cylindrically-shaped interior shell segment that is sized to fit inside and rotate within the exterior shell cavity such that threading along an interior shell inner surface engages corresponding threading along an outer surface of the driver whereby rotation of the interior shell segment via an associated access port causes linear movement of the driver along the handle longitudinal axis.

13. A catheter actuation handle assembly according to any of paragraphs 1-12 above wherein the handle assembly is characterized by at least two moveable components comprising drivers of substantially the same size and shape, each associated with a driver-distal member control wire that connects the moveable driver to a distally-extending member, and also an actuation component that comprises a pair of mating interior shell halves forming a cylindrically-shaped interior shell segment that is sized to fit inside and rotate within the exterior shell cavity such that first threading along a first portion of the interior shell inner surface engages corresponding threading along an outer surface of a first moveable driver, and second threading of a different orientation direction and/or a different pitch than the first threading along a second portion of the interior shell inner surface engages corresponding threading along an outer surface of a second moveable driver, whereby rotation of the interior shell segment housing the first and second moveable drivers via an associated access port results in linear movement of both moveable drivers but in different directions or at different rates of movement.

14. A catheter actuation handle assembly according to any of paragraphs 1-13 above wherein the handle assembly is characterized by a plurality of corresponding threaded exterior shell screw holes are located along the periphery of the exterior shell halves, and a set of screws sized and threaded to match the exterior shell screw holes is used to fasten the exterior shell halves together.

15. A catheter actuation handle assembly according to any of paragraphs 1-14 above wherein the handle assembly is characterized by an actuation component comprising a pair of mating interior shell halves forming a cylindrically-shaped interior shell segment that is sized to fit inside and rotate within the exterior shell cavity such that threading along an interior shell inner surface engages corresponding threading along an outer surface of a moveable component comprising a driver whereby rotation of the interior shell segment via an associated access port causes linear movement of the driver along the handle longitudinal axis, and also a plurality of corresponding threaded interior shell screw holes are located along the periphery of the interior shell halves, and a set of screws sized and threaded to match the interior shell screw holes is used to fasten the interior shell halves together.

16. A catheter actuation handle assembly according to any of paragraphs 1-15 above wherein the handle assembly is characterized by an actuation component comprising a pair of mating interior shell halves forming a cylindrically-shaped interior shell segment that is sized to fit inside and rotate within the exterior shell cavity such that threading along an interior shell inner surface engages corresponding threading along an outer surface of a moveable component comprising a driver whereby rotation of the interior shell segment via an associated access port causes linear movement of the driver along the handle longitudinal axis, and also one or more knob features along the outer surface of the interior shell at locations where the knob features align with and project at least partly into or through an access port.

17. A catheter actuation handle assembly according to any of paragraphs 1-16 above wherein the handle assembly is characterized by at least two moveable components comprising drivers of substantially the same size and shape, each associated with a driver-distal member control wire that connects the moveable driver to a distally-extending member, and further where each of the moveable drivers is located in a separate, independently rotatable interior shell segment such that it can be actuated independently of the other moveable drivers, and also a knob feature along the outer surface of each interior shell segment that houses a moveable driver where the knob feature aligns with and projects at least partly into or through an access port.

18. A catheter actuation handle assembly according to any of paragraphs 1-17 above wherein the handle assembly is characterized by at least two moveable components comprising drivers of substantially the same size and shape, each associated with a driver-distal member control wire that connects the moveable driver to a distally-extending member, and further where each of the moveable drivers is located in a separate, independently rotatable interior shell segment such that it can be actuated independently of the other moveable drivers, and also a slotted support washer positioned between at least two of the separate interior shell segments with slots sized and located to accommodate a pair of guide rails that extend between the most proximal and the most distal drivers.

19. A catheter actuation handle assembly according to any of paragraphs 1-18 above wherein the handle assembly is characterized by at least two moveable components comprising drivers of substantially the same size and shape, each associated with a driver-distal member control wire that connects the moveable driver to a distally-extending member, and further where each of the moveable drivers is located in a separate, independently rotatable interior shell segment such that it can be actuated independently of the other moveable drivers, and also a distal-end stationary driver positioned distal of the most distal of the moveable drivers, a proximal-end stationary driver positioned proximal of the most proximal of the moveable drivers, and a mid-body stationary driver positioned between the most distal moveable driver and the most proximal moveable driver.

20. A catheter actuation handle assembly according to any of paragraphs 1-19 above wherein the handle assembly is characterized by at least two moveable components comprising drivers of substantially the same size and shape, each associated with a driver-distal member control wire that connects the moveable driver to a distally-extending member, and further where each of the moveable drivers is located in a separate, independently rotatable interior shell segment such that it can be actuated independently of the other moveable drivers, and also a distal-end stationary driver positioned distal of the most distal of the moveable drivers, a proximal-end stationary driver positioned proximal of the most proximal of the moveable drivers, and a mid-body stationary driver positioned between the most distal moveable driver and the most proximal moveable driver, and also slotted support washers positioned between the interior shell segment housing the mid-body stationary driver and the distal and proximal interior shell segments housing, respectively, the distal moveable driver and the proximal moveable driver, each slotted support washer having slots sized and located to accommodate a pair of guide rails that extend between the most proximal and the most distal drivers.

21. A catheter actuation handle assembly according to any of paragraphs 1-20 above wherein the handle assembly is characterized by a moveable driver-distal member control wire that connects at least one moveable driver to a distally-extending member.

22. A catheter actuation handle assembly according to any of paragraphs 1-21 above wherein the handle assembly is characterized by at least one stationary driver located within the exterior shell cavity together with a stationary driver-distal member control wire that connects at least one of the stationary drivers to a distally-extending member.

23. A catheter actuation handle assembly according to any of paragraphs 1-22 above wherein the handle assembly is characterized by at least one stationary driver located within the exterior shell cavity together with a stationary driver-distal member control wire that connects at least one of the stationary drivers to a distally-extending member, and also a moveable driver-distal member control wire that connects at least one moveable driver to a distally-extending member.

24. A catheter actuation handle assembly according to any of paragraphs 1-23 above wherein the handle assembly is characterized by a moveable driver-distal member control wire that connects at least one moveable driver to a distally-extending member, and at least one stationary driver connected to a distally-extending member.

25. A catheter actuation handle assembly according to any of paragraphs 1-24 above wherein the handle assembly is characterized by a moveable driver-distal member control wire that connects at least one moveable driver to a distally-extending member, and a guide sleeve that houses at least a portion of the moveable driver-distal member control wire that is in the exterior shell cavity.

26. A catheter actuation handle assembly according to any of paragraphs 1-25 above wherein the handle assembly is characterized by an actuation component comprising a pair of mating interior shell halves forming a cylindrically-shaped interior shell segment that is sized to fit inside and rotate within the exterior shell cavity such that threading along an interior shell inner surface engages corresponding threading along an outer surface of a moveable component comprising a driver whereby rotation of the interior shell segment via an associated access port causes linear movement of the driver along the handle longitudinal axis, and the moveable driver comprises a threaded driver end having a first diameter with circumferential threading along the outer surface and axially-oriented guide rail slots intersecting the threading, and an unthreaded protrusion driver end having a second diameter, smaller than the first diameter, and with axially-oriented control wire slots along the outer surface, and a moveable driver-distal member control wire that passes through one of the driver's control wire slots in connecting the moveable driver to a distally-extending member.

27. A catheter actuation handle assembly according to any of paragraphs 1-26 above wherein the handle assembly is characterized by a fluid line that extends from outside the actuation handle housing into the interior shell cavity, where it connects to a driver and/or to a distally-extending member and/or to another fluid tube that connects to a driver and/or a distally-extending member.

28. A catheter actuation handle assembly according to any of paragraphs 1-27 above wherein the handle assembly is characterized by an actuation component that comprises a pair of mating interior shell halves forming a cylindrically-shaped interior shell segment that is sized to fit inside and rotate within the exterior shell cavity and a moveable component comprising a driver housed inside and attached to the interior shell segment whereby rotation of the interior shell segment via an associated access port results in rotation of the moveable driver and the distally-extending members connected to the driver.

29. A catheter actuation handle assembly according to any of paragraphs 1-28 above wherein the handle assembly is characterized by a moveable component comprising a rotatable cam member pivoted inside the exterior shell cavity to rotate about an axis that is orthogonal to the handle longitudinal axis; a pair of opposing cam-distal member control wires that connect different portions of the cam member to a distally-extending member; and, a knob feature connected to the cam member and projecting through an access port that aligns with the cam member.

30. A catheter actuation handle assembly according to any of paragraphs 1-29 above wherein the handle assembly is characterized by a moveable component comprising a moveable driver located within the exterior shell cavity; a pair of driver-distal member control wires providing two connections between the driver and a distally-extending member, where a first of the control wires connects directly to a connection point of the driver, while a second of the control wires is routed through the exterior shell cavity to a location proximal of the driver where it loops around and returns to the driver connection point; and, an actuation component for translating the driver distally or proximally along the axis of the actuation handle.

31. A catheter actuation handle assembly according to any of paragraphs 1-30 above wherein the handle assembly is characterized by a moveable component comprising a rotational knob adapted to rotate about the axis of the actuation handle at an axial location where it aligns with an access port; a pair of knob-distal member control wires providing two connections between the rotational knob and a distally-extending member; and, an actuation component comprising a geometrical feature along the circumference of the rotational knob that facilitates rotation of the knob via the access port.

32. A catheter actuation handle assembly according to any of paragraphs 1-31 above wherein the handle assembly is characterized by a moveable component comprising a pivot assembly adapted to pivot about a point along the axis of the actuation handle at an axial location where it aligns with an access port; two or more pivot-distal member control wires providing multiple connections between the pivot assembly and a distally-extending member; and, an actuation component comprising a plate member exterior of the actuation handle housing that is connected to the pivot assembly via the access port.

33. A catheter actuation handle assembly according to any of paragraphs 1-32 above wherein the handle assembly is characterized by a spring-loaded component comprising a compressed spring element located within the exterior shell cavity and connected to a distally-extending member such that release of the compressed spring element via an access port drives the distally-extending member rapidly and forcefully in the distal direction, in combination with a spring-release mechanism.

34. A catheter actuation handle assembly according to any of paragraphs 1-33 above wherein the handle assembly is characterized by an actuation component comprising a positioning button having upper and lower sides that slidably rides in an access port comprising an elongated slot in the actuation handle housing that parallels the handle longitudinal axis, also where the upper side of the positioning button is exterior to the actuation handle housing while the lower side is within the exterior shell cavity, and the lower side has a geometrical feature that can releasably engage the moveable driver for linear movement along the longitudinal axis.

35. A catheter actuation handle assembly according to any of paragraphs 1-34 above wherein the handle assembly is characterized by an actuation handle housing comprising two pairs of mating exterior shell halves, one of which is a distal exterior shell segment and the other a proximal exterior shell segment that houses the moveable component, where the distal segment and the proximal segment are axially spatially separated but connected such that the distal segment can be articulated relative to the longitudinal axis of the proximal segment, and also where the spatial separation constitutes the access port.

36. A catheter actuation handle assembly according to any of paragraphs 1-35 above where the handle assembly is sized and shaped to be held in and controlled by a single human hand.

37. A catheter actuation handle assembly according to any of paragraphs 1-36 above wherein the exterior shell halves, or the interior shell halves or both are symmetrical relative to the corresponding mating shell half.

38. A catheter actuation system comprising a catheter handle assembly according to any of paragraphs 1-37 above in combination with a fluid/flush line and a fluid source that provides fluid communication between a fluid source that is exterior to the actuation handle housing and a location inside the exterior shell cavity.

39. A catheter actuation system according to any of paragraphs 1-38 above wherein the fluid/flush line provides a fluid communication to the proximal end of a catheter lumen of a distally-extending member.

40. A method for assembling a catheter actuation handle assembly according to any of paragraphs 1-39 above comprising the sequential steps of: nesting a lower interior shell half segment inside a lower exterior shell half segment whereby geometrical features along the outer surface of the lower interior shell half segment nest inside correspondingly sized and shaped geometrical features along the inner surface of the lower exterior shell half; positioning actuation handle components that are housed inside the exterior shell cavity, including one or more substantially identical externally-threaded drivers or other moveable components, in the open interior of the nested lower half shells; connecting proximal ends of one or more distally-extending members or control wires connected to distally-extending members to one or more of the drivers or moveable components; mating the upper interior shell half segment(s) with the corresponding lower interior shell half segment(s); mating the upper exterior shell half segment(s) with the lower exterior shell half segment(s); and securing the upper and lower exterior shell halves together to complete the actuation handle assembly.

41. A method for using a catheter actuation handle assembly according to any of paragraphs 1-39 above comprising the steps of manipulating the one or more actuation components of the assembly via the one or more access ports to actuate one or more of the moveable components causing translation, articulation and/or rotation of the distally-extending members that are attached to the moveable components.

42. A method according to paragraph 41 above wherein one or more control wires extending from moveable components of the assembly to distally-extending members are manipulated using an actuation component of the assembly to effect articulation of the distally-extending members in two or more directions.

43. A reconfigurable catheter handle assembly comprising:
an exterior shell having an elongated shape formed about a common axis;
an interior shell comprising at least two disengageable interior shell segments removably contained within the exterior shell, wherein: when within the exterior shell, the interior shell is rotatable about the common axis, and when not within the exterior shell, the at least two interior shell segments are configured to disengage; and,
one or more moveable components configured to be installed within one or both of the interior and exterior shells and, when installed in the interior shell, configured to control at least one member extending distally from the catheter handle in response to rotation of the interior shell contained within the exterior shell.

44. The catheter handle assembly according to paragraph 43 above, wherein the exterior shell comprises at least two disengageable exterior shell pieces configured to disengage to enable insertion and removal of the interior shell and/or of the moveable components, the actuation components and the connection components going to distally-extending members.

45. The catheter handle assembly according to any of paragraphs 43-44 above, wherein one or more access ports are formed within the exterior shell, the one or more access ports being configured to allow for communication between a user and the exterior shell cavity, such communication enabling actuation of the moveable components.

46. The catheter handle assembly according to any of paragraphs 43-45 above, wherein at least two access ports are formed within the exterior shell, each access port configured to allow for communication between a user and one of at least two independently rotatable segments of an interior shell.

47. The catheter handle assembly according to any of paragraphs 43-46 above, wherein an interior shell comprises an internal threaded surface and one or more driver components comprise an external threaded surface configured to mate with the internal threaded surface of the interior shell.

48. The catheter handle assembly according to any of paragraphs 43-47 above, wherein at least a driver component is configured to translate forward and backward within an interior shell in response to rotation of the interior shell.

49. The catheter handle assembly according to any of paragraphs 43-48 above, wherein one or more driver components is configured to remain relatively fixed in position with respect to the exterior shell while an interior shell is rotated within the exterior shell.

50. The catheter handle assembly according to any of paragraphs 43-49 above, further comprising one or more anti-rotation constraints configured to maintain one or more driver components in a relatively fixed position with respect to the exterior shell.

51. The catheter handle assembly according to any of paragraphs 43-50 above, wherein the one or more anti-rotation constraints comprise one or more guide rails configured for insertion between the one or more driver components and an interior shell.

52. The catheter handle assembly according to any of paragraphs 43-51 above, wherein the one or more guide rails are configured to couple to proximal and distal ends of the exterior shell.

53. The catheter handle assembly according to any of paragraphs 43-52 above, wherein an interior shell comprises a plurality of interior shell segments, wherein at least one interior shell segment is configured to function independently from one or more other interior shell segments.

54. The catheter handle assembly according to any of paragraphs 43-53 above, wherein the catheter handle assembly is configured to control a plurality of distally-extending members and each independently functioning interior shell segment is configured to control a different one or more of the plurality of distally-extending members.

55. The catheter handle assembly according to any of paragraphs 43-54 above, wherein at least one driver component is disposed in each independently functioning interior shell segment.

56. The catheter handle assembly according to any of paragraphs 43-55 above, further comprising one or more support members disposed between axially-aligned interior shell segments.

57. The catheter handle assembly according to any of paragraphs 43-56 above, wherein the one or more support members comprise at least one support washer disposed between two driver components.

58. A method for using a catheter actuation handle assembly where the assembly comprises the following elements:
an exterior shell having an elongated shape formed about a common axis;
an interior shell comprising at least two disengageable interior shell segments removably contained within the exterior shell, wherein: when within the exterior shell, the interior shell is rotatable about the common axis, and when not within the exterior shell, the at least two interior shell segments are configured to disengage; and,
one or more moveable components configured to be installed within one or both of the interior and exterior shells and, when installed in the interior shell, configured and/or connected so as to control at least one member extending distally from the catheter handle in response to movement of the interior shell contained within the exterior shell;
the method comprising manipulating one or more of the members extending distally from the catheter handle by accessing the interior shell via at least an access port in the exterior shell and thereby translating and/or rotating the interior shell to in turn cause translation, articulation and/or rotation of the members extending distally.

59. A catheter handle assembly as shown and described in the figures.

60. A catheter system as shown and described in the figures.

61. A catheter handle kit as shown and described in the figures.

62. A method of assembling a catheter handle as shown and described in the figures.

63. A method of controlling one or more distally-extending members using a catheter actuation handle assembly as shown and described in the figures.

These and other benefits, advantages and applications for the technologies of this invention will be better understood by the following detailed description and the accompanying drawings.

DESCRIPTION OF THE INVENTION EMBODIMENTS

Figure 1:
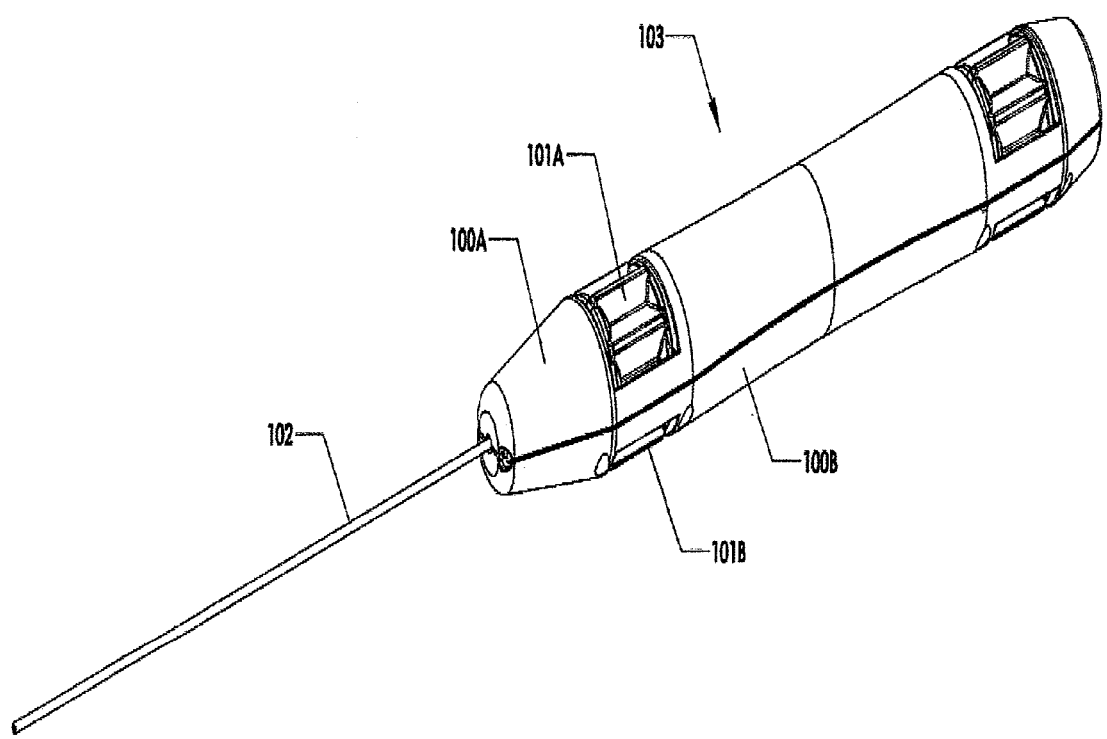
FIG. 1 is a schematic exterior isometric view of an embodiment of a catheter actuation handle assembly according to the invention.
Figure 2:
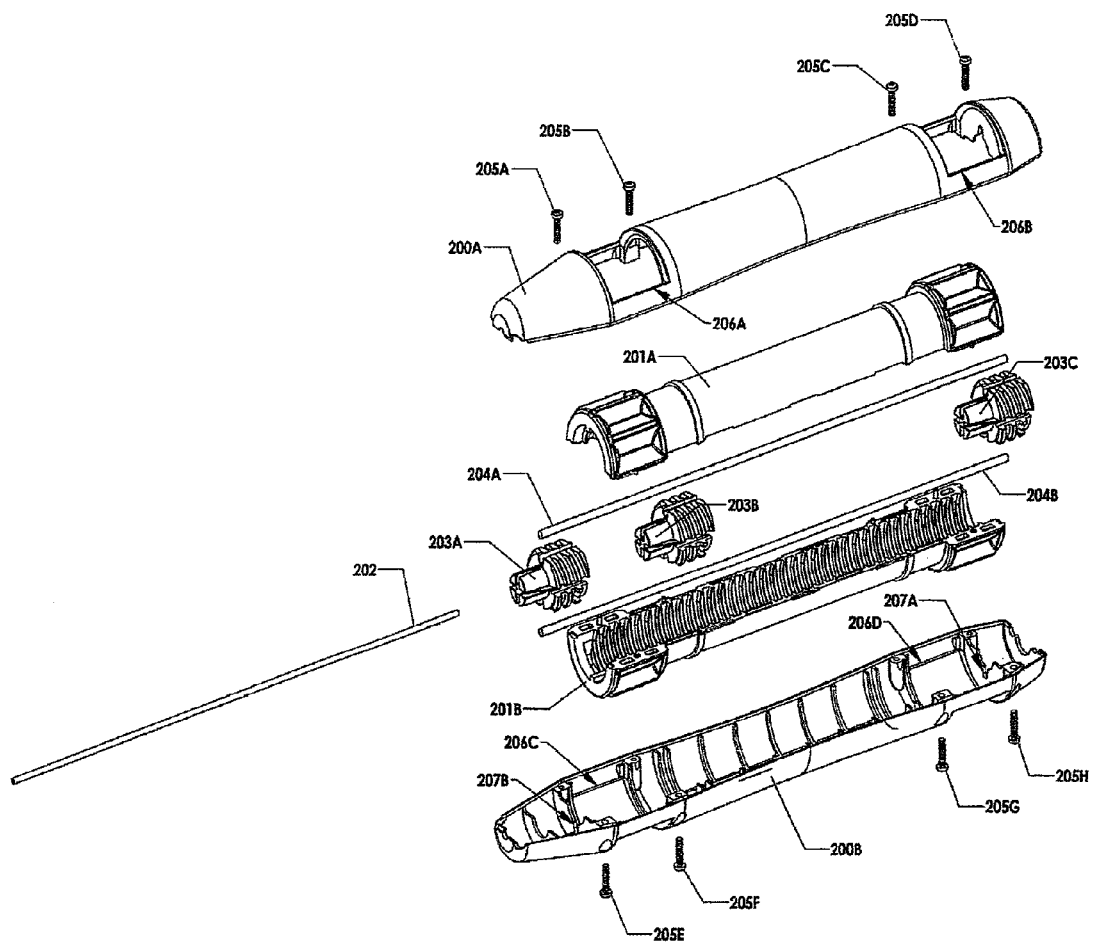
FIG. 2 is a schematic fully-exploded isometric view of an embodiment of a catheter actuation handle assembly according to an embodiment of the invention showing the several component parts for a "full-stroke" invention configuration.

As shown in the invention embodiment of FIGS. 1 and 2, the catheter actuation handle 103 comprises an exterior shell or actuation handle housing consisting of two symmetrical and mating exterior shell halves 100A, 100B (FIG. 1) or 200A, 200B (FIG. 2) and an interior shell or interior housing consisting of two mating interior shell halves 101A, 101B (FIG. 1) or 201A, 201B (FIG. 2) (which can be symmetrical in some invention embodiments), the interior shell being sized to nest inside of and to engage with the exterior shell halves. The catheter handle 103 also connects to and interacts with one or more distally-extending members (for example 102 in FIG. 1 or 202 in FIG. 2) to effect their actuation. As can be better understood by the exploded view shown in FIG. 2, the invention embodiment of FIGS. 1 and 2 also employs one or more externally threaded driver components (for short "drivers") 203A, 203B, 203C. The drivers 203A, 203B and 203C are substantially identical in size and shape, sized to fit inside the interior and exterior shells, and configured to function in various ways in cooperation with other internal components and/or with the geometry of the interior or exterior shells of the actuation handle.

Specifically, in this invention embodiment, threads along the surface of a driver mate with corresponding threading along the inner surfaces of the two interior shell halves. The drivers also interface with distally-extending members (such as members 202) and also correspond to and/or engage with geometric features along either the exterior shell halves 200A, 200B and/or along the interior shell halves 201A, 201B in order to position and actuate the distally-extending members 202 relative to each other and relative to the actuation handle. The interior and exterior shells and the drivers may be fabricated from any suitable materials, e.g., plastic materials, that satisfy conventional structural and other performance characteristics for catheters. In FIG. 2, reference numerals 205A through 205H identify screws used to secure exterior shell halves 200A and 200B to each other after the various internal components of the apparatus are assembled. It will be understood that alternative shell-half connection/fastening systems, for example a "snap-fit" system utilizing correspondingly sized and positioned pins or projections and matching pin holes along the mating edges of two shell halves, can be substituted for the connection system of screws and screw holes illustrated in FIG. 2.

The actuation handle as described above has one or more relief windows/communication apertures/access ports (for example 206A, 206B, 206C, 206D in FIG. 2), which terms are used interchangeably herein, in exterior shell halves 200A, 200B that allow for communication between a user and the interior shell when the catheter handle is fully assembled. Rotation of the interior shell via manual actuation through the access ports 206A, 206B, 206C, 206D activates the engaged threads between the interior shell halves 201A, 201B and corresponding external threading of driver 203B, thereby translating rotary motion of the interior shell into linear motion of the driver 203B inside the interior shell. Because driver 203B is connected to the distally-extending member(s) 202, movement of driver 203B actuates member(s) 202 in some way, depending on how these components are connected.

As can be understood from FIG. 2, the drivers 203A, 203B and 203C are employed as multipurpose components located within the interior region of the catheter handle. These drivers are preferably substantially identical and interchangeable, and they can usefully be positioned at a variety of locations and in distal-facing or proximal-facing orientations along the interior region. This flexibility in the positioning and orientation of the interchangeable drivers contributes to the unique modularity of the catheter actuation handles of this invention.

As further illustrated by FIG. 2, the present invention employs guide rails 204A, 204B, typically fabricated from a metal such as stainless steel, that create an anti-rotation constraint of one or more of drivers 203A, 203B, 203C relative to the exterior shell. Because the drivers are constrained from rotating but are threadably engaged with the interior shell, actuation (rotation) of the interior shell achieves relative motion of the drivers along the catheter handle axis. For example, rotation of the interior shell causes driver 203B (which is threadably engaged with the threads of the interior shell), and a wire that connects driver 203B to the distally-extending members, or any elements connected to the distally-extending members, to move forward and/or backward relative to the handle. As described hereinafter, how such forward or backward movement actuates the distally-extending members depends on how those members are connected to one or more of the drivers or to other parts of the catheter actuation handle. As can be understood from FIGS. 2, 10 and 11, the driver anti-rotation constraint is achieved by virtue of guide rails 204A, 204B (FIG. 2), 1001A, 1001B (FIG. 10) engaging proximal and distal exterior shell half slots 207A, 207B (FIG. 2) and driver slots 1101A, 1101B, 1101C, 1101D (FIG. 11) as needed to achieve a sufficient degree of anti-rotation resistance.

Figure 3:
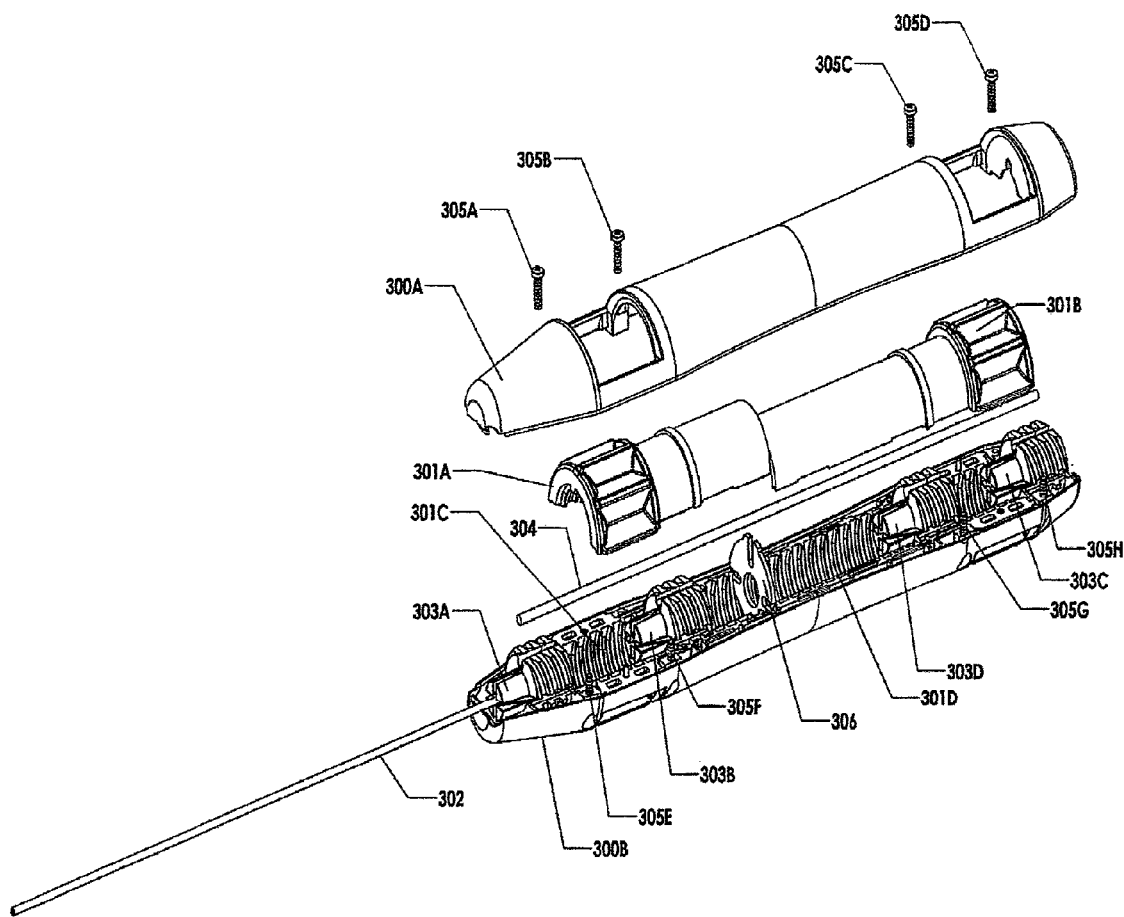
FIG. 3 is a schematic partially-exploded isometric view of an embodiment of a catheter actuation handle assembly according to an embodiment of the invention showing the several component parts for a "split-lead" invention configuration.

As illustrated in FIG. 3, other embodiments of the present invention can embody a split-lead configuration in which the interior shell halves 201A, 201B (FIG. 2) are sectioned into at least two (e.g., proximal and distal) interior shell segments to accommodate independent functioning of each end, resulting in interior shell half segments 301A, 301B, 301C, 301D. In FIG. 3, reference numerals 300A and 300B identify the exterior shell halves, and reference numeral 302 identifies the distally-extending member(s).

In this FIG. 3 configuration of a catheter actuation handle, an intermediately positioned support washer 306 can be employed to provide added support for the guide rails 304. Anti-rotation resistance is provided by virtue of the support washer's interlock with a slot-type geometric feature along the inner surface of the exterior shell or housing (refer to FIG. 12 for an illustration of this support washer/exterior shell engagement). The apparatus of FIG. 3 includes four drivers—a distal-end driver 303A, a proximal-end driver 303C, and two intermediately positioned drivers 303B and 303D. The support washer 306 can further be rigidly attached to the guide rails 304 such that it provides a discrete separation along the interior region of the catheter handle for containment of the intermediately positioned drivers 303B, 303D operating inside the distinct and independently actuatable distal and proximal segments of the interior shell, as defined by the distal and proximal interior shell half segments 301A, 301C and 301B, 301D, respectively. In FIG. 3, reference numerals 305A through 305H identify screws used to secure exterior shell halves 300A and 300B to each other after the various components of the apparatus are assembled. It will be understood that alternative shell-half connection/fastening systems, for example a "snap-fit" system utilizing correspondingly sized and positioned pins or projections and matching pin holes along the mating edges of two shell halves, can be substituted for the connection system of screws and screw holes illustrated in FIG. 3.

Figure 4:
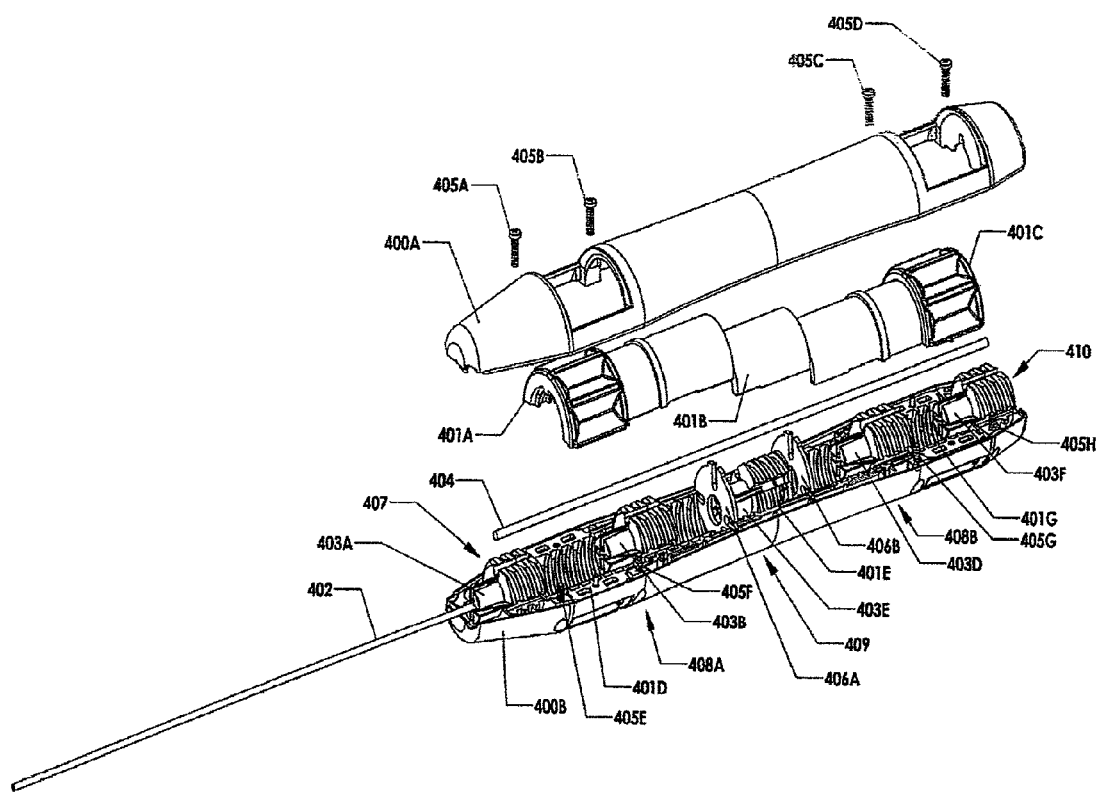
FIG. 4 is another schematic partially-exploded isometric view of an embodiment of a catheter actuation handle assembly showing what might be called a "mid-body" invention configuration.

FIG. 4 shows a catheter actuation handle in a mid-body configuration, a configuration which facilitates illustrating various common locations for usefully positioning one or more of the moveable and stationary drivers 403A, 403B, 403D, 403E, 403F. The interior shell of FIG. 4 comprises three interior shell segments—a proximal-end interior shell segment, a distal-end interior shell segment, and a middle interior shell segment.

A first useful driver position 407 for locating a stationary driver 403A is in the interior of the distal nose section (which may advantageously be tapered in the distal direction as shown in the drawings) of the actuation handle. In location 407, driver 403A is inside the exterior shell of the actuation handle, but it is at a location that is distal of the distal end of the interior shell. In this location, the natural orientation of driver 403A is with the slotted driver protrusion 1100 (FIG. 11) oriented distally along the axis of the actuation handle. In this driver position, the driver 403A is stationary. As a stationary driver, driver 403A can act as an origination point for a stationary distally-extending member (such as member 402), or for elements stemming from member 402. In this driver position, driver 403A can also be used for sealing and flushing any telescoping members that may be located inside a stationary distally-extending member. The exterior shell halves 400A, 400B are designed (i.e., shaped and sized) such that a driver 403A at location 407 could be oriented in either direction—i.e., with the slotted driver protrusion 1100 (FIG. 11) facing distally or proximally—according to which assembly orientation was considered advantageous for a desired functionality.

A second useful driver position 408A and/or 408B for locating a moveable driver in the embodiment of FIG. 4 is internal to the interior shell halves 201A, 201B (FIG. 2), or in one or more segments of the interior shell halves (if the interior shell comprises a plurality of interior shell segments), e.g., the respective distal, middle and proximal segments. As described in connection with the invention embodiments of FIGS. 1 to 3, the threads of the drivers 403B and 403D engage the corresponding threads along the inner sides of the two associated segments of the interior shell. This second useful driver position is represented by either moveable driver 403B at location 408A, or by moveable driver 403D at location 408B, or, in some embodiments, by having both of drivers 403B and 403D. This driver positioning facilitates linear translation of at least some of the distally-extending members (such as member 402, or elements stemming from member 402), by establishing a connection (e.g., a wire connection) between a distally-extending member and at least one of these moveable drivers 403B, 403D. A symmetric thread pattern in some embodiments allows for orientation of the drivers 403B, 403D in either axial direction, i.e., with the slotted driver protrusion portions 1100 (FIG. 11) of the moveable drivers facing distally or proximally, according to which orientation yields a desired functionality.

Figure 12:
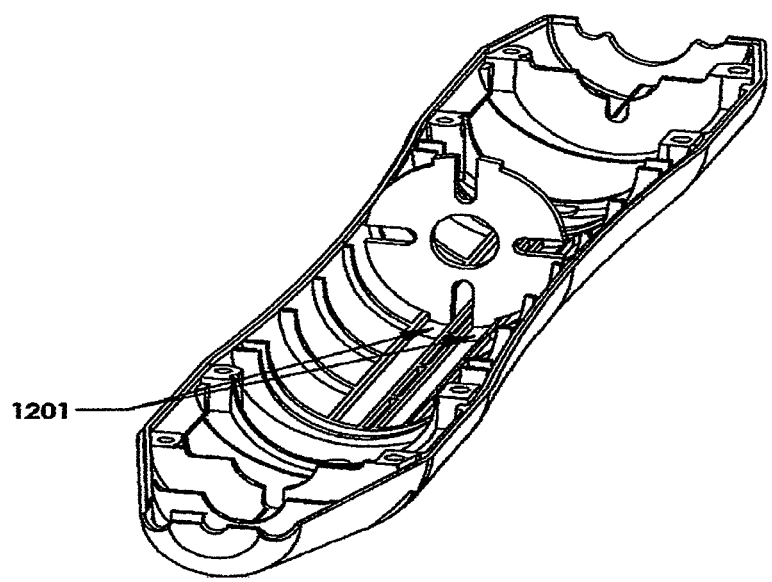
FIG. 12 is a schematic isometric view of the interior of one of the two exterior shell halves that, when mated with a corresponding exterior shell half, comprises the exterior shell or housing of a catheter actuation handle, shown in combination with an internal support washer and also showing a support washer alignment slot formed along the inner surface of the exterior shell half that is used to properly position the washer inside the exterior shell.

A third useful driver position 409 for locating a stationary driver 403E is rigidly attached to a middle segment of the segmented interior shell, e.g., inside interior shell half segments 401B, 401E that have been sectioned away from the respective proximal and distal ends of the interior shell such that this middle interior shell segment can be isolated inside the catheter handle where it is constrained by a pair of support washers 406A, 406B, which register it relative to the guide rails 404 and the exterior shell halves 400A, 400B. As best seen in FIG. 12, there are exterior shell half registration slots 1201, defined by ribs or ridges along the inner surface of the exterior shell halves, which allow for this isolated middle interior shell segment to be placed at an infinitely variable location along any part of the portion of the exterior shell cavity that includes the slots 1201 as a geometrical feature along the inner surface of the exterior shell. Placing a threaded driver 403E in this third driver position 409 fixes it axially relative to the exterior shell halves 400A, 400B by virtue of the constrained interior shell halves 401B, 401E, such that a stationary distally-extending member, or elements stemming from such a distally-extending member, can be rigidly attached to the stationary driver 403E making that distally-extending member accessible for flushing (similar to the preceding description of the utility of stationary driver 403A located in the first position 407).

This mid-handle, rigidly attached, non-rotating positioning of stationary driver 403E in location 409 can also enable further actuation of other distally-extending members, or of elements stemming from such members, relative to a member that is rigidly attached to driver 403E positioned at location 409. An example of the utility of this configuration would be a distally-extending catheter shaft that is rigidly terminated at a driver 403E positioned at location 409 and that also has an articulation control/pull wire such as 508 (shown in FIG. 5) extending further in the proximal direction and connected to a second driver 403D oriented as described and positioned in location 408B, such that rotation of the segmented interior shell halves 401C, 401F translates the control/pull wire forward and backward inside the actuation handle, which in turn articulates the catheter shaft that is rigidly terminated at driver 403E positioned at location 409.

Figure 10:
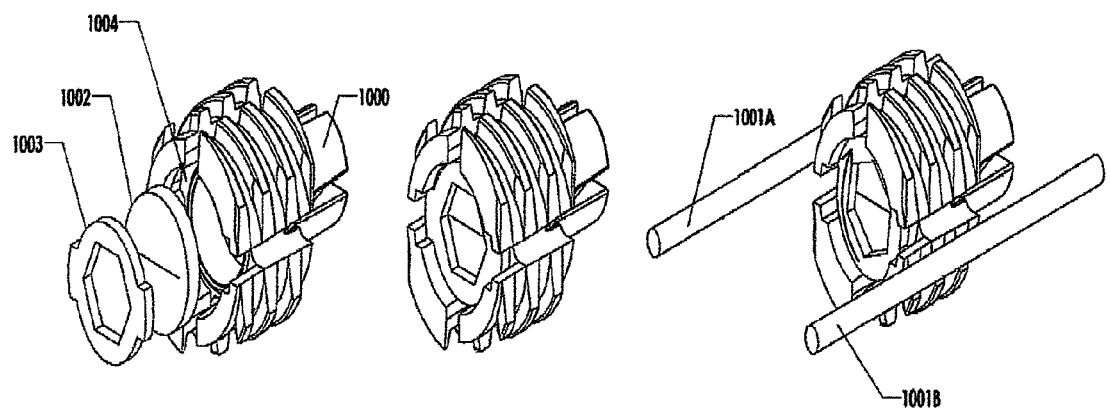
FIG. 10 consists of three sequential (left to right) schematic views of a diaphragm seal component according to an embodiment of the invention illustrating how a diaphragm seal is loaded into a recess or pocket in an end face of a threaded driver component, then locked in place by a tabbed washer, and finally rotationally-inhibited by the insertion of guide rails, all of these being components that are located in an interior region of a catheter actuation handle according to the invention.

A fourth useful driver position 410 for locating a stationary driver 403F is in the proximal end of the actuation handle that is proximal of the proximal end of the interior shell and in a pocket defined by geometrical features along the inner surface of the exterior shell such that driver 403F is rigidly oriented relative to the exterior shell and the guide rails. A stationary driver 403F positioned at location 410 can serve as a proximal end termination point for distally-extending members that are axially fixed relative to the actuation handle. Similar to the preceding description of the utility of driver 403A at location 407, the driver 403F and the associated seal assembly (as shown in FIG. 10) allows for isolation and flushing of a catheter lumen that is at least one of the distally-extending members and attached at its proximal end to the driver 403F at location 410. The driver 403F can, similar to other drivers, be oriented in either axial direction, i.e., with the slotted driver protrusion 1100 (FIG. 11) facing distally or proximally if such orientation yields a desired functionality.

Drivers 403A, 403B, 403D, 403E, and 403F are preferably substantially identical and interchangeable. They are designed in a maximum material condition such that the axially-oriented through-hole 1103 (FIG. 11) can be post-processed to a desired dimension. This customization of the through-hole size enables a driver to be adapted to interface with a range of catheter shaft (and associated catheter lumen) sizes, for example any catheter shaft with an outer dimension between about 5 F and 24 F, although larger or smaller sizes could also be accommodated. In FIG. 4, reference numerals 405A through 405II identify screws used to secure exterior shell halves 400A and 400B to each other after the various internal components of the apparatus are assembled. It will be understood that alternative shell-half connection/fastening systems, for example a "snap-fit" system utilizing correspondingly sized and positioned pins or projections and matching pin holes along the mating edges of two shell halves, can be substituted for the connection system of screws and screw holes illustrated in FIG. 4.

Figure 5:
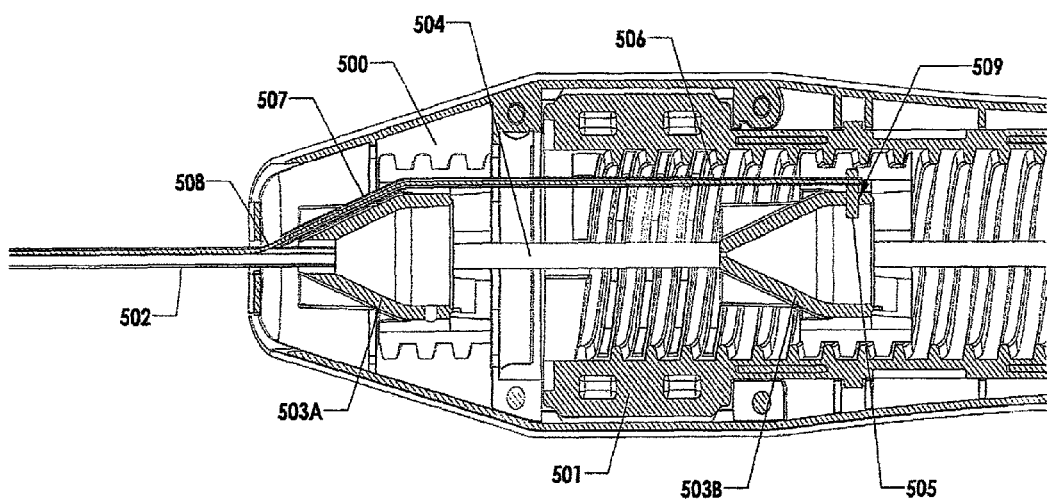
FIG. 5 is a schematic cross-sectional view of the distal segment of an embodiment of a catheter actuation handle assembly illustrating an invention embodiment whereby the handle can be used for actuating an articulation control/pull wire extending distally from the distal end of the handle.

The enlarged cross-section of the distal end of a catheter actuation handle shown in FIG. 5 illustrates an embodiment for articulation of a distally-extending member, such as member 502. In FIG. 5, reference numeral 500 identifies a sectional view of an exterior shell, and reference numeral 501 identifies a sectional view of an interior shell. In this articulation embodiment, a catheter shaft 502 is rigidly terminated at a driver 503A (positioned at the first driver position, namely location 407 (FIG. 4), as described above). An articulation pull wire 508 that emanates from the side wall of the distally-extending catheter shaft 502 is routed around the driver 503A (that the catheter shaft 502 is attached to), and it then extends along the periphery of the interior of the actuation handle to the driver 503B (that is located in the second driver position, namely location 408A) where the articulation pull wire 508 is rigidly attached. Reference numeral 504 identifies a guide rail (typically employed in pairs) that is used for positioning, securing and properly orienting various internal components as described hereinafter. This apparatus configuration also has the following features and functionalities:

(a) A pair of telescoping hypotubes (distal support tube 507 and proximal support tube 506) are used as guide sleeves to support the articulation pull wire 508 so it can smoothly translate back and forth within the interior of the actuation handle. In the configuration shown, the distal support tube 507 is positioned distally and is rigidly attached to an outer surface of driver 503A (that is located in the first driver position). The proximal support tube 506 is located more proximally and is rigidly attached to the articulation pull wire 508 and to dowel pin 505 via a solder joint, or press fit, or set screw engagement, or by similar means.

(b) The dowel pin 505 that is rigidly attached to the articulation pull wire 508 and to proximal support tube 506 is loaded through a cross-hole 509 which is oriented orthogonally relative to the longitudinal axis of the actuation handle and also relative to the through-hole 1103 (cross-hole 509 in FIG. 5 corresponds to cross-hole 1104 in FIG. 11) in the driver 503B (which is located in the second driver position). This engagement configuration properly orients the dowel pin 505, the proximal support tube 506 and the articulation pull wire 508. Attachment by means of adhesive, press fit, compressive set screw, threaded engagement or any other such fastening mechanism, secures the dowel pin 505, and therefore also the proximal support tube 506 and the articulation pull wire 508, to the driver 503B such that translation of driver 503B (for example by rotation of the interior shell) back and forth within the interior of the actuation handle actuates the articulation pull wire 508 along its length and thereby articulates the catheter shaft 502.

Figure 11:
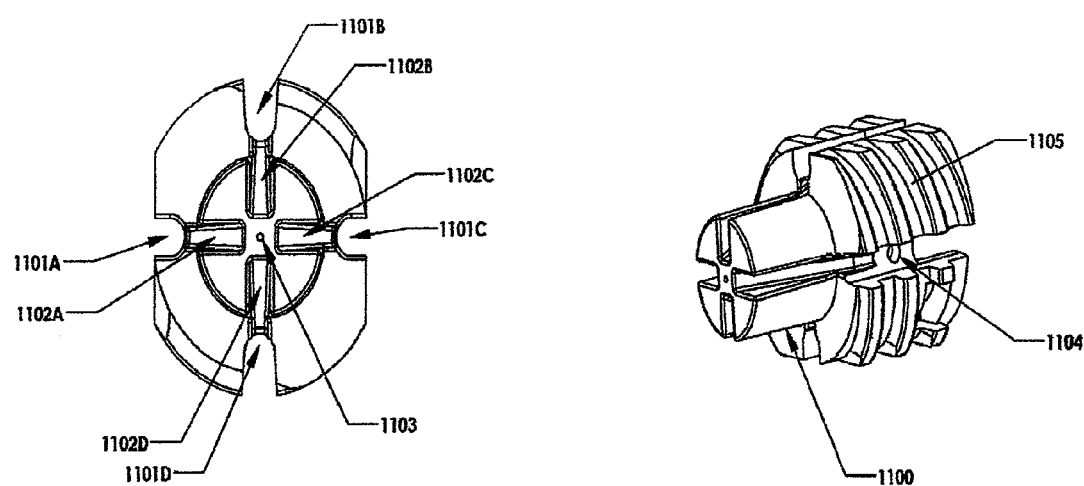
FIG. 11 consists of a schematic front view and a schematic isometric view of a threaded driver component that is sized to fit inside an interior region of a catheter actuation handle according to the invention and is configured to function in various ways in cooperation with other internal components of the catheter actuation handle and with geometrical features of other components of the catheter actuation handle.

(c) As shown in FIG. 11, the slotted driver protrusion portion 1100 of the driver 1105 (which is preferably substantially identical to the other driver components of this invention) has four protrusion slots (which are also referred to herein as "control wire slots") 1102A, 1102B, 1102C, 1102D (shown at 90° angular increments around the circumference of the protrusion portion) that are clocked such that they lead into corresponding slotted breaks 1101A, 1101B, 1101C, 1101D in the threads along the externally-threaded portion of driver 1105. These protrusion slots can be used to guide an articulation pull wire (driver-distal member control wire), such as pull wire 508 (FIG. 5), and support tubes 506, 507 such that the articulation pull wire 508 could be routed through any of the four protrusion slots (control wire slots) according to the desired orientation of the catheter apparatus and the associated plane of articulation of the catheter shaft relative to the actuation handle.

Figure 6:
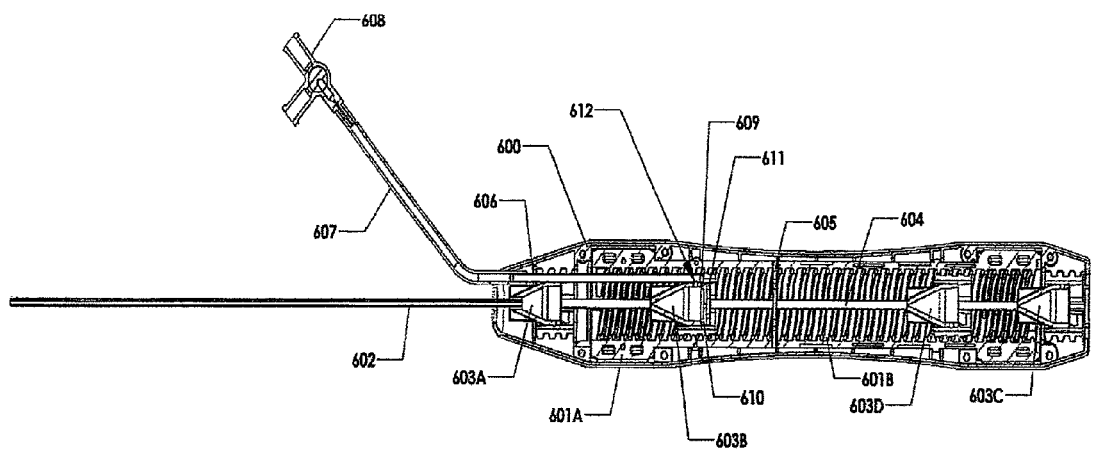
FIG. 6 is a schematic cross-sectional view of an embodiment of a catheter actuation handle assembly wherein an external fluid flush line is fluidically coupled to an interior region of the handle at its distal end.
Figure 7:
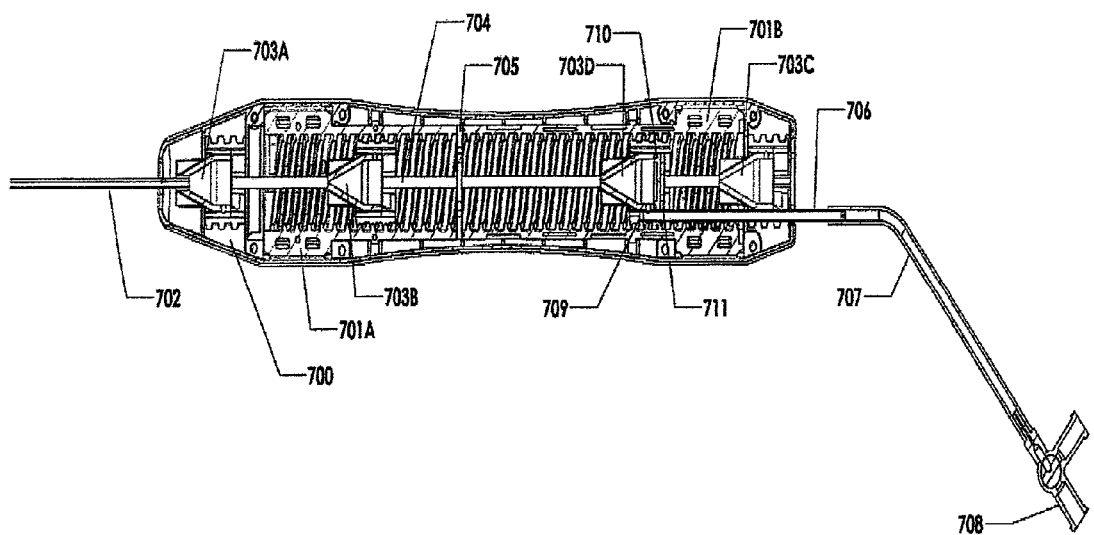
FIG. 7 is a schematic cross-sectional view of an embodiment of a catheter actuation handle assembly wherein an external fluid flush line is fluidically coupled to an interior region of the handle at its proximal end.
Figure 8:
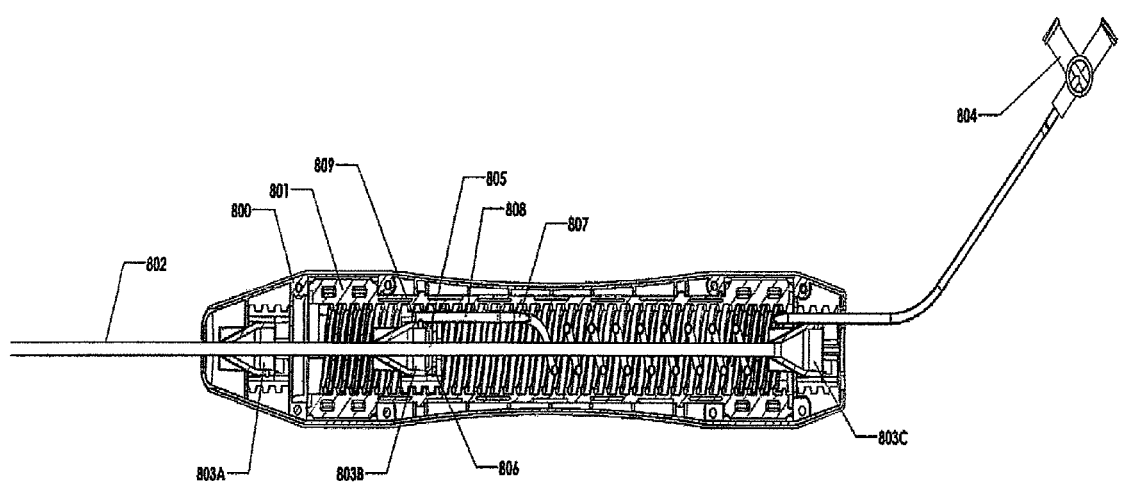
FIG. 8 is a schematic cross-sectional view of an embodiment of a catheter actuation handle assembly having a "full-stroke" configuration in combination with an external fluid flush line that extends into an interior region of the handle at the proximal end of the handle housing and then continues through the interior of the handle in a coiled configuration.
Figure 9:
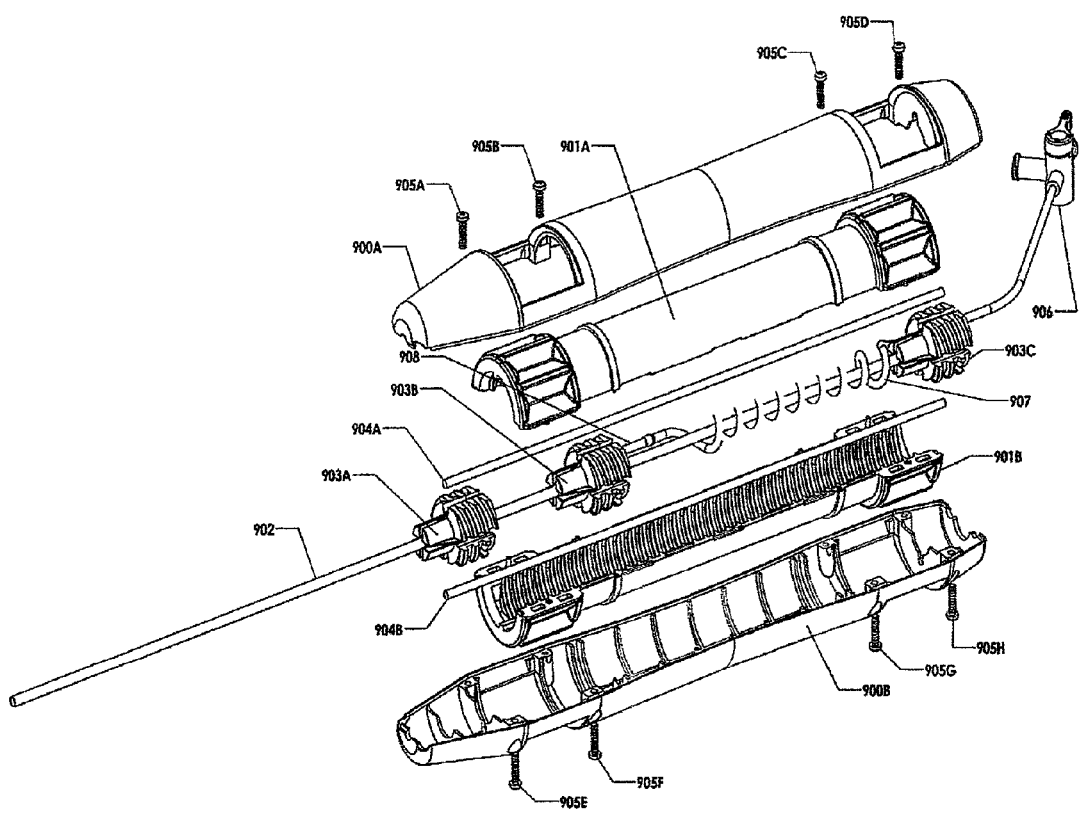
FIG. 9 is a schematic fully-exploded isometric view of an embodiment of a catheter actuation handle assembly having a "full-stroke" configuration in combination with an external fluid flush line that extends into an interior region of the handle at the proximal end of the handle housing and then continues through the interior of the handle in a coiled configuration.

FIGS. 6, 7, 8 and 9 illustrate the modular fashion in which fluid/flush lines 607, 707, 807, 907, respectively, can be routed into and through the interior of the actuation handle to access the drivers 603A, 603B, 603C, 603D (in FIG. 6), 703A, 703B, 703C, 703D (in FIG. 7), 803A, 803B, 803C (in FIG. 8), and 903A, 903B, 903C (in FIG. 9), where those drivers can be located in one or more of the four driver positions described previously in connection with FIG. 4. In FIGS. 6, 7 and 8, reference numerals 600, 700 and 800, respectively, identify sectional views of exterior shells. In FIGS. 6 and 7, reference numerals 601A, 601B and 701A, 701B, respectively, identify interior shell halves. In FIG. 8, reference numeral 801 identifies an interior shell half. In FIG. 9, reference numerals 900A and 900B identify exterior shell halves. In FIGS. 6-9, reference numerals 602, 702, 802 and 902, respectively, identify distally-extending members. In FIGS. 6, 7 and 9, reference numerals 604, 704 and 904A, 904B, respectively, identify guide rails.

In FIGS. 6 and 7, reference numerals 605 and 705, respectively, identify support washers. Also in FIGS. 6 and 7, the tabbed locking washers 610 and 710, respectively, secure compliant diaphragm seals 609 and 709, respectively, into drivers 603B and 703D, respectively. FIGS. 6 and 7 also show plug-in ports 611 and 711, respectively, for connecting the semi-rigid tubes 606 and 706, respectively, to create complete fluid paths in conjunction with fluid/flush lines 607 and 707, respectively.

In FIGS. 8 and 9, reference numerals 804 and 906, respectively, identify termination manifolds (which may comprise, for example, a stopcock) for the proximal ends of the flexible tubing (fluid/flush) lines 807 and 907, respectively. Also shown in FIG. 8 is a diaphragm seal 805 (corresponding to seal members 609 and 709, respectively, in FIGS. 6 and 7), a tabbed locking washer 806 (corresponding to tabbed locking washers 610 and 710, respectively, in FIGS. 6 and 7), and a plug-in port 809 (corresponding to plug-in ports 611 and 711, respectively, in FIGS. 6 and 7). In FIG. 9, reference numerals 905A through 905H identify screws used to secure exterior shell halves 900A and 900B to each other after the various internal components of the apparatus are assembled. It will be understood that alternative shell-half connection/fastening systems, for example a "snap-fit" system utilizing correspondingly sized and positioned pins or projections and matching pin holes along the mating edges of two shell halves, can be substituted for the connection system of screws and screw holes illustrated in FIG. 9.

The fluid/flush lines as illustrated in FIGS. 6-9 can enter (leave) the interior region at either the distal or proximal end of the actuation handle according to desired functionality and access considerations. The various fluid/flush lines can be used to provide a suitable flushing fluid to the interior of the actuation handle and also to provide a flushing fluid, or any other suitable fluid (e.g., a heat transfer fluid, saline solution, medicine, etc.) to one or more of the distally-extending catheter shafts or other distally-extending members that originate from the interior of the actuation handle.

A rigid or semi-rigid tube 606, 706, 808, 908 (respectively in FIGS. 6, 7, 8 and 9) may be employed in the actuation handle interior region for connecting a fluid/flush line to an associated driver. FIG. 6 shows how a transversely-oriented cross-hole (509 in FIGS. 5 and 1104 in FIG. 11) in the driver 603B is aligned with a corresponding cross-hole 612 in the rigid or semi-rigid tube 606 such that fluid communication is established between the two conduits. The rigid or semi-rigid tube 606 is permanently attached to the driver 603B such that it establishes a fluid seal and defines the fluid path by which fluid/flushing media can be introduced. According to FIGS. 6 and 7, the rigid or semi-rigid tube 606, 706 can be oriented to extend distally (as shown in FIG. 6) or proximally (as shown in FIG. 7) relative to the associated driver 603B, 703D, according to desired function and point of juncture with the actuation handle.

For "fixed" locations for positioning a stationary driver (i.e., the first, third and fourth driver positions as described above in connection with FIG. 4), the rigid or semi-rigid tube 606, 706 can act as a transfer lumen by which fluid is carried from a driver 603A, 603C, 703A, 703C to an exit location at either end of the actuation handle. After exiting the interior of the actuation handle, the fluid/flush line 606, 706 can be extended by connection to a flexible tubing line 607, 707 terminating into a manifold, such as a stopcock 608, 708, or otherwise accessed for further fluid communication. With respect to a moveable driver in the second position (as described above in connection with FIG. 4), because such a driver is subject to axial translation, the rigid or semi-rigid tube 606, 706, 808, 908 is attached and paired to the driver 603B, 703D, 803B, 903B such that it can translate back and forth together with the driver 603B, 703D, 803B, 903B. In this embodiment, there are at least two alternative options for extended fluid transfer as described below:

Option 1 (FIGS. 6 and 7): The rigid or semi-rigid tube 606, 706 in the interior of the actuation handle can be extended directly out from either end of the actuation handle, where it can be further extended by connection to a flexible exterior tubing line 607, 707, terminating into a manifold, such as a stopcock 608, 708, or otherwise accessed for further fluid communication.

Option 2 (FIGS. 8 and 9): The rigid or semi-rigid tube 808, 908 in the interior of the actuation handle can be transitioned to a flexible interior tube 807, 907 that is coiled inside the interior shell halves 901A, 901B in such a fashion that it can expand and contract along the length of the handle interior as the associated moveable driver 803B, 903B translates inside the interior shell halves 901A, 901B. Furthermore, the flexible tube 807, 907 coil could be coiled only for a portion of its length such that it exits the actuation handle at either its distal or proximal end where it can transition to an exterior straight flexible segment (shown but not numbered) which can be accessed for further fluid communication, e.g., via a manifold/stopcock 804, 906. An advantage of this configuration (Option 2) is that the external portion of the fluid/flush line would not be required to translate back and forth together with movement of its associated driver 803B, 903B.

FIG. 10 shows a sealing mechanism employed with the driver 1000 at any location in the handle interior that requires sealing and/or flushing of a lumen, such as a lumen of a distally-extending catheter shaft. The primary components of the sealing mechanism are the diaphragm seal 1002 (fabricated from a compliant material and cross-cut to elastically seal against catheter elements that pass through it) and the tabbed locking washer 1003 that compresses the diaphragm seal 1002 into place. In one invention embodiment, during assembly the diaphragm seal 1002 is loaded into an appropriately sized and shaped pocket or recess 1004 that is formed in the non-protruding axial driver face of the driver, i.e., the driver face that is opposite from the axial driver face from which the slotted driver protrusion 1000 (or 1100 in FIG. 11) projects. The tabbed locking washer 1003 is sized and shaped to fit into pocket 1004. The locking washer 1003 is loaded into pocket 1004 over diaphragm seal 1002, compressed into pocket 1004, and rotated (e.g., clockwise) using a suitable tool into a locked position where it holds the diaphragm seal 1002 in compression. Because of the orientation of the washer tabs and the locked location of the washer 1003, this driver/seal/washer assembly can be assembled as the actuation handle is being constructed without the use of any permanent fasteners. As the actuation handle is constructed, however, the washer 1003 and diaphragm 1002 become constrained within the associated driver pocket 1004 once guide rails 1001A, 1001B are loaded into place. Ultimately the components of the driver/seal/washer assembly are fixed in place by the surrounding elements of the fully assembled actuation handle. This allows for a stable, yet non-permanent means of seal assembly that facilitates reworking and reconfiguring a catheter actuation handle of this invention for a different application or functionality. This is another novel feature of the present invention that contributes to the modularity of these catheter actuation handles.

A number of other specific advantageous embodiments of the present invention will now be described with reference to FIGS. 13-27.

Figure 13:
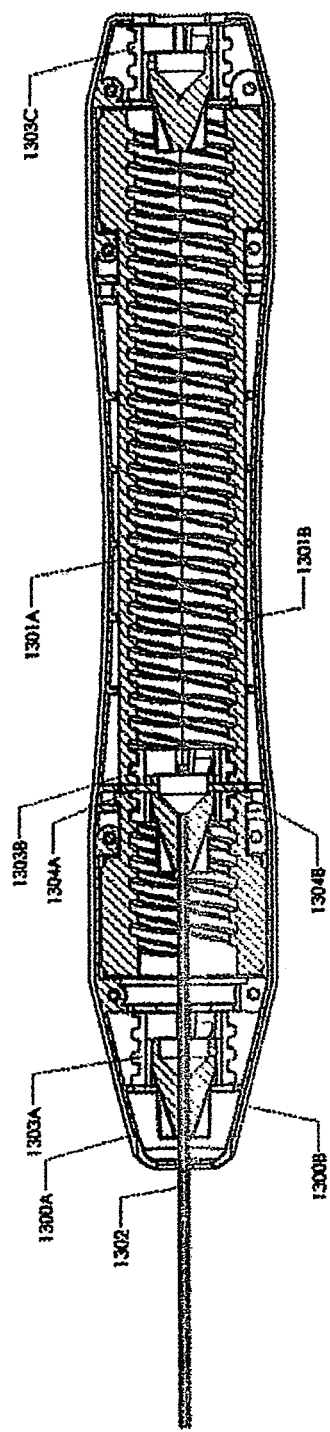
FIG. 13 is a schematic cross-sectional side view of an embodiment of a catheter actuation handle assembly according to an embodiment of the invention showing the several component parts for a type of "rotary" invention configuration.

FIG. 13 is a schematic cross-sectional side view of an embodiment of a catheter actuation handle according to an embodiment of the invention showing the several component parts for what can be called a "rotary" invention configuration. In FIG. 13, reference numerals 1300A and 1300B identify cross-sections of exterior shell halves, and reference numerals 1303A and 1303C are stationary driver components.

As seen in FIG. 13, a moveable driver 1303B is located within and attached to an interior shell/housing segment 1301A, 1301B such that driver 1303B is rotationally locked relative to that interior shell/housing segment 1301A, 1301B. In this configuration, rotation of the interior shell/housing segment 1301A, 1301B about the longitudinal axis of the actuation handle transfers that rotation directly to the driver 1303B and, thereby, to any distally-extending member(s) 1302 attached to driver 1303B. The driver 1303B and interior shell/housing segment 1301A, 1301B may be connected by means of adhesive attachment, pinning (as illustrated in FIG. 13, showing pins 1304A, 1304B), set screw engagement, heat-staking, welding, or any other type of connection that results in sufficient rotational coupling of these components. By actuating the moveable component, which is the interior shell/housing segment 1301A, 1301B, for example via an actuation component (not shown in FIG. 13 but similar to several configurations earlier described and as illustrated in previous drawings), a user can rotationally control distally-extending member(s) 1302 such that those distally-extending member(s) 1302 are advantageously clocked or swept through an arc according to their desired positioning and function for a given application.

Figure 14:
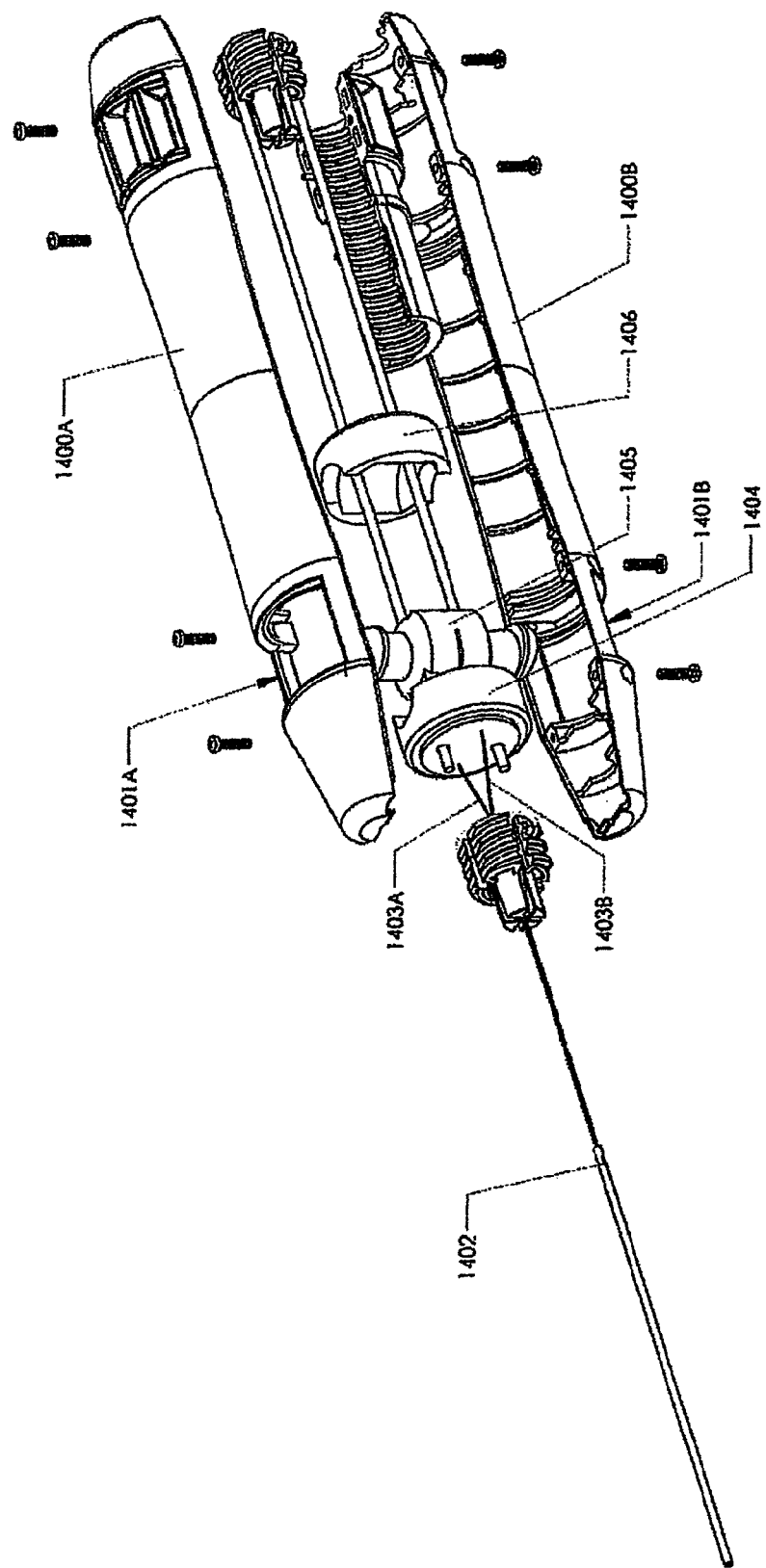
FIG. 14 is a schematic fully-exploded isometric view of an embodiment of a catheter actuation handle assembly according to an embodiment of the invention showing the several component parts for a type of "bilateral swivel" invention configuration.

FIG. 14 is a schematic fully-exploded isometric view of an embodiment of a catheter actuation handle according to an embodiment of the invention showing the several component parts for a type of "bilateral swivel" invention configuration.

Figure 15:
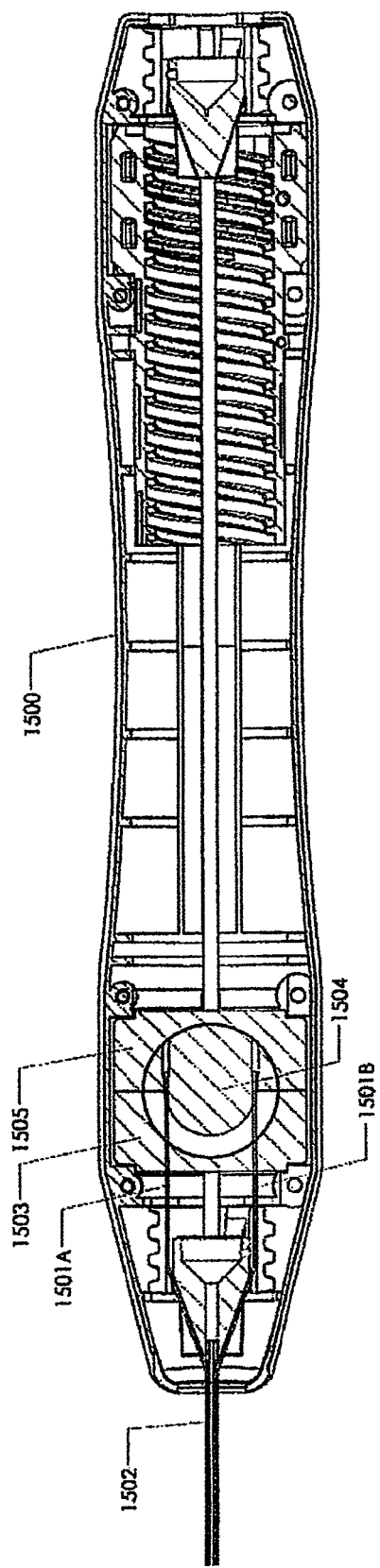
FIG. 15 is a schematic cross-sectional top view of the "bilateral swivel" invention configuration of FIG. 14 wherein two opposing pull wires are actuated to achieve bilateral articulation of a distally-extending member.

FIG. 15 is a schematic cross-sectional top view of the "bilateral swivel" invention configuration of FIG. 14 wherein two opposing control/pull wires are actuated to achieve bilateral articulation of a distally-extending member. In FIG. 14, reference numerals 1400A and 1400B identify exterior shell halves. The screws for securing these two exterior shell halves to each other are shown but not numbered. It will be understood that alternative shell-half connection/fastening systems, for example a "snap-fit" system utilizing correspondingly sized and positioned pins or projections and matching pin holes along the mating edges of two shell halves, can be substituted for the connection system of screws and screw holes illustrated in FIG. 14. In FIG. 15, reference numeral 1500 is a sectional view of the exterior shell.

In particular, FIGS. 14 and 15 illustrate an alternative articulation mechanism for achieving a "bilateral swivel" type of bilateral actuation of distally-extending member(s) 1402/1502. In this embodiment, a type of rotating knob-and-cam assembly comprising components 1404, 1405, 1406/1503, 1504, 1505 is aligned with a communication aperture/access port in the exterior housing, namely with exterior housing relief windows 1401A, 1401B in FIG. 14, such that the rotatable cam member 1405/1504 (contained between the cam housing members 1404 and 1406) can be rotated about a cam axis that is at an angle (e.g., orthogonal) relative to the actuation handle longitudinal axis. With this embodiment, a user can access and rotate the cam member 1405/1504 by means of the rotating knob portion of the cam assembly so as to simultaneously actuate two control/pull wires 1403A, 1403B/1501A, 1501B which are connected to distally-extending member(s) 1402/1502. When cam member 1405/1504 is rotated in one direction, the rotating cam assembly 1404, 1405, 1406/1503, 1504, 1505 applies tension to one control/pull wire (also referred to herein as a cam-distal member control wire) while simultaneously relieving tension, or applying compression, to the other control/pull wire. Rotating cam member 1405/1504 in the opposite direction achieves a mirrored result. The rotating cam assembly 1404, 1405, 1406/1503, 1504, 1505 is shown aligning with the more distal of two sets of access ports in the actuation handle housing, but it could alternatively be oriented to align with the more proximal access ports or with another such set of apertures if there are more than two.

For bilateral articulation embodiments involving two opposed control/pull wires, such as described above in connection with FIGS. 14 and 15 (and also in connection with some subsequent drawings), a "slack recovery" principle plays a role in the functionality of the apparatus. Because two opposed control/pull wires are generally employed to articulate the same distally-extending member in opposite directions, they have a paired function. When one wire is tensioned (the "active" wire) and its length within a catheter that extends distally from the actuation handle is reduced, the resulting flexion draws in the opposite control/pull wire (the "inactive" wire), adding to its length within the catheter that extends distally from the actuation handle. The tension on the active wire, however, tends to naturally recover the slack of the inactive wire by virtue of their mechanical communication. Such behavior means that a bilateral articulation mechanism in accordance with this invention does not necessarily have to actively manage the return slack of the inactive wire. Allowing the inactive wire to passively return to its original position when rotational force on the active wire is released may often be sufficient.

Figure 16:
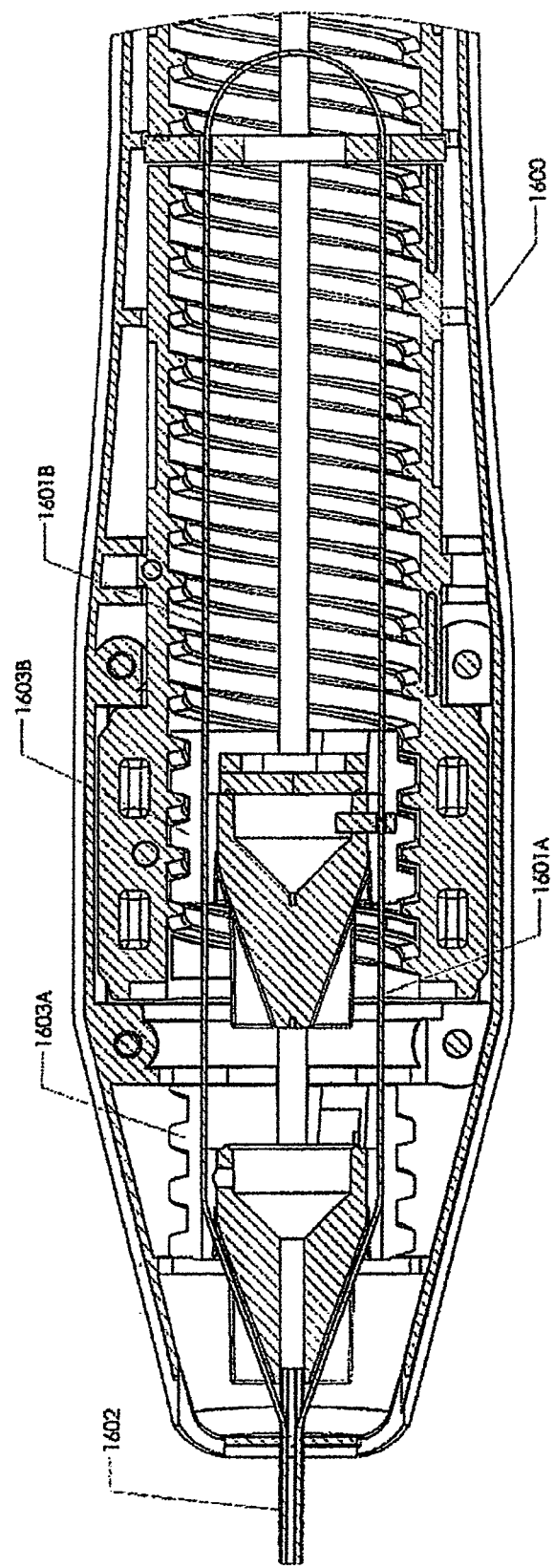
FIG. 16 is a schematic cross-sectional side view of an embodiment of a catheter actuation handle assembly according to an embodiment of the invention showing the several component parts for a type of "looped wire" invention configuration.

FIG. 16 is a schematic cross-sectional side view of an embodiment of a catheter actuation handle according to an embodiment of the invention showing the several component parts for what can be called a "looped wire" invention configuration. In FIG. 16, reference numeral 1600 is a sectional view of the exterior shell, and 1603A is a stationary driver.

In FIG. 16, one control/pull wire 1601A is routed through the interior of the actuation handle and attached directly to an actuatable looped wire driver 1603B (as previously described in connection with FIG. 5), while a second control/pull wire 1601B makes an approximate 180 degree loop within the exterior shell cavity at a location proximal relative to the position of the looped wire driver 1603B such that it can be attached to the same driver 1603B by a similar means as the first control/pull wire. This "looped wire" configuration enables concurrent actuation of the two control/pull wires 1601A, 1601B in opposite relative directions by linear translation of driver 1603B along the axis of the actuation handle such that distally-extending member 1602 can be articulated in different directions (that is about +180° to about −180°, more or less) relative to the longitudinal axis.

Figure 17:
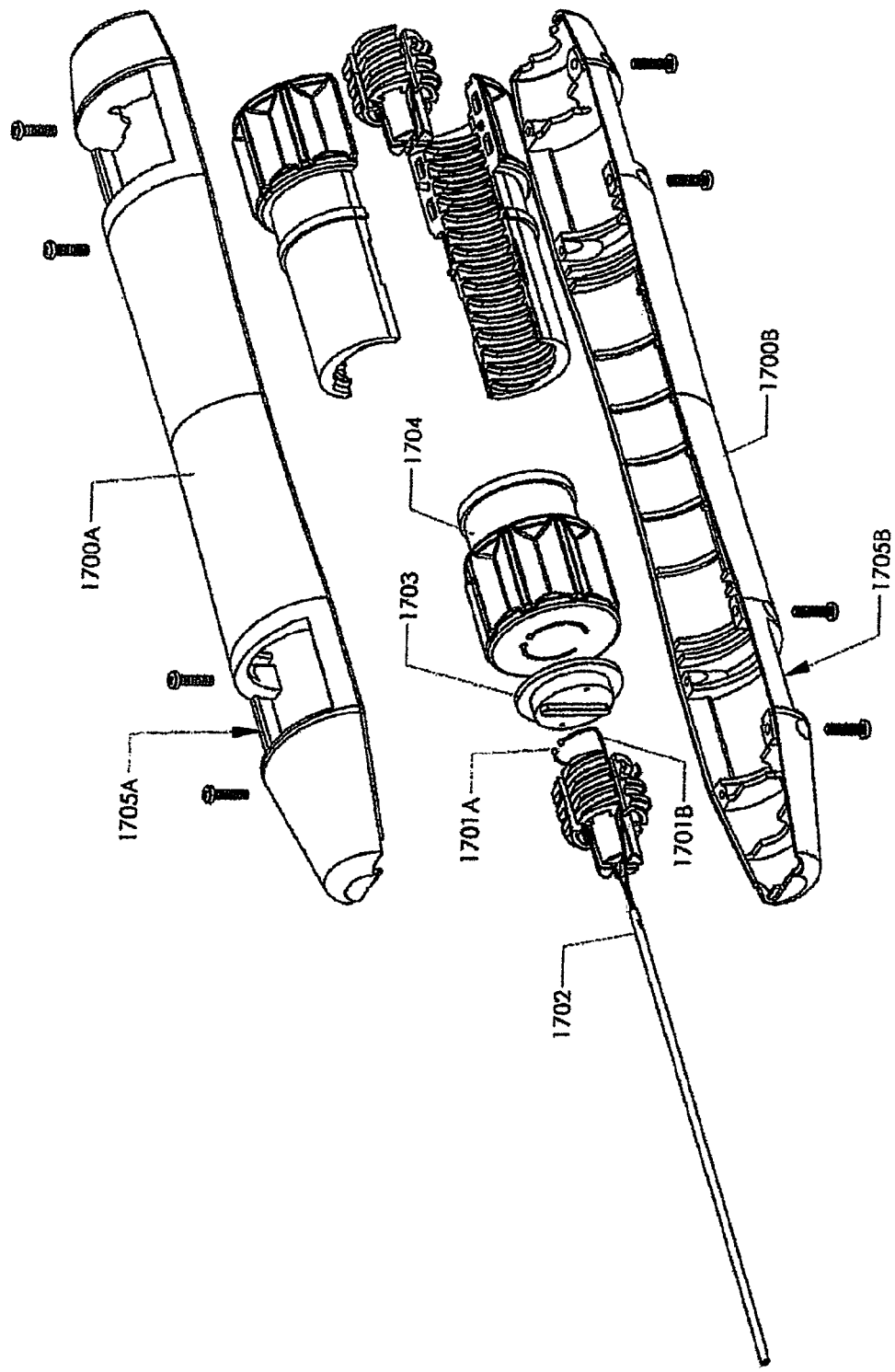
FIG. 17 is a schematic fully-exploded isometric view of an embodiment of a catheter actuation handle assembly according to an embodiment of the invention showing the several component parts for a type of "rotational bilateral" invention configuration.
Figure 18:
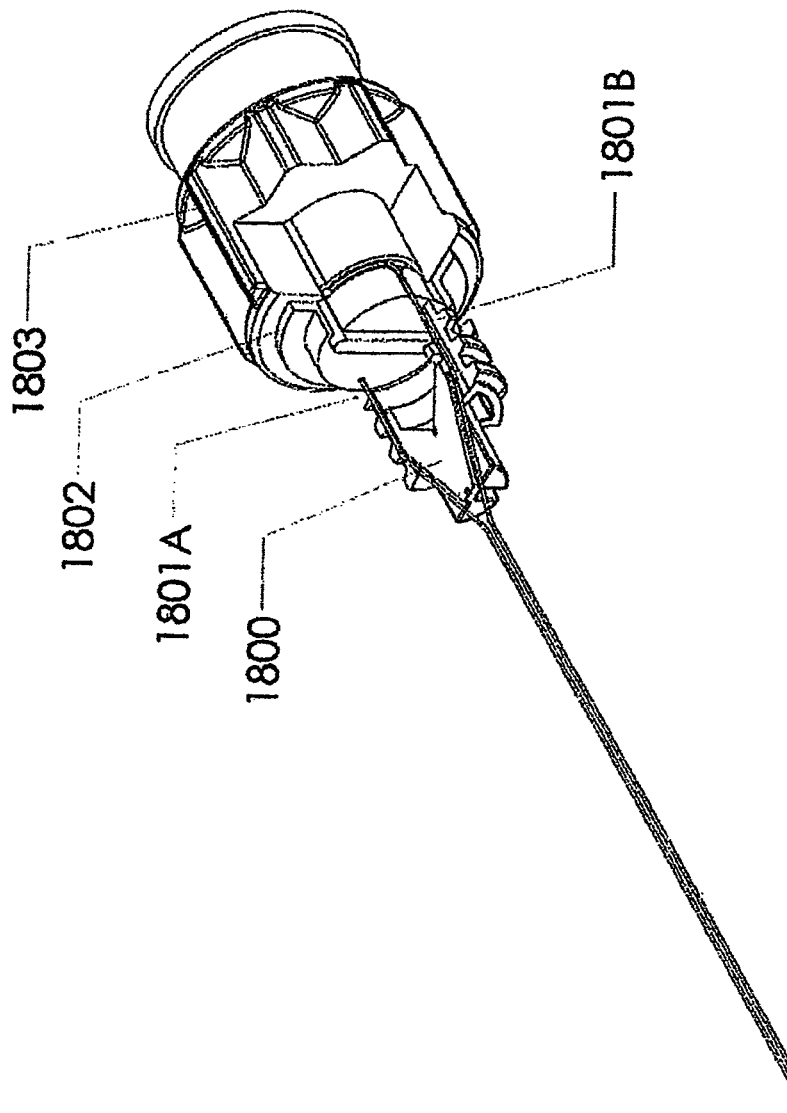
FIG. 18 is a schematic partially-sectioned isometric view of an interior portion of the "rotational bilateral" invention configuration of FIG. 17.

FIG. 17 is a schematic fully-exploded isometric view of an embodiment of a catheter actuation handle according to an embodiment of the invention showing the several component parts for a type of "rotational bilateral" invention configuration. In FIG. 17, reference numerals 1700A and 1700B identify exterior shell halves, and 1702 identifies the distally-extending catheter members. In FIG. 17, the screws for securing the two exterior shell halves to each other are shown but not numbered. It will be understood that alternative shell-half connection/fastening systems, for example a "snap-fit" system utilizing correspondingly sized and positioned pins or projections and matching pin holes along the mating edges of two shell halves, can be substituted for the connection system of screws and screw holes illustrated in FIG. 17. Also in FIG. 17, reference numerals 1705A and 1705B are communication apertures/access ports through which the rotational knob 1704 is accessed for initiating bilateral articulation. FIG. 18 is a schematic partially sectioned isometric view of the "rotational bilateral" invention configuration of FIG. 17 wherein reference numeral 1800 is a stationary driver.

In particular, FIGS. 17 and 18 show yet another means of achieving bilateral articulation using what can be called a "rotational bilateral" invention configuration. This invention embodiment represents a specific application of articulation mechanisms that were generically described earlier in this application for achieving some form of bilateral or multilateral articulation of distally-extending members. In FIGS. 17 and 18, two control/pull wires (which are also referred to herein as "knob-distal member control wires") 1701A, 1701B/1801A, 1801B are attached to a rotational knob/positioning plate assembly such that the wires are guided along the periphery of the interior of the actuation handle according to their respective rotational positions (according to the slots in the associated distal end driver). In this embodiment, the control/pull wires are then threaded through a positioning plate 1703/1802, which constrains the entry point of each control/pull wire. Then, each control/pull wire is attached at a location inside the rotational knob 1704/1803 located proximally of the positioning plate such that the amount of control/pull wire that extends distally through the positioning plate 1703/1802 can be selectively lengthened or shortened based on the angle of rotation of the rotational knob 1704/1803.

Figure 19:
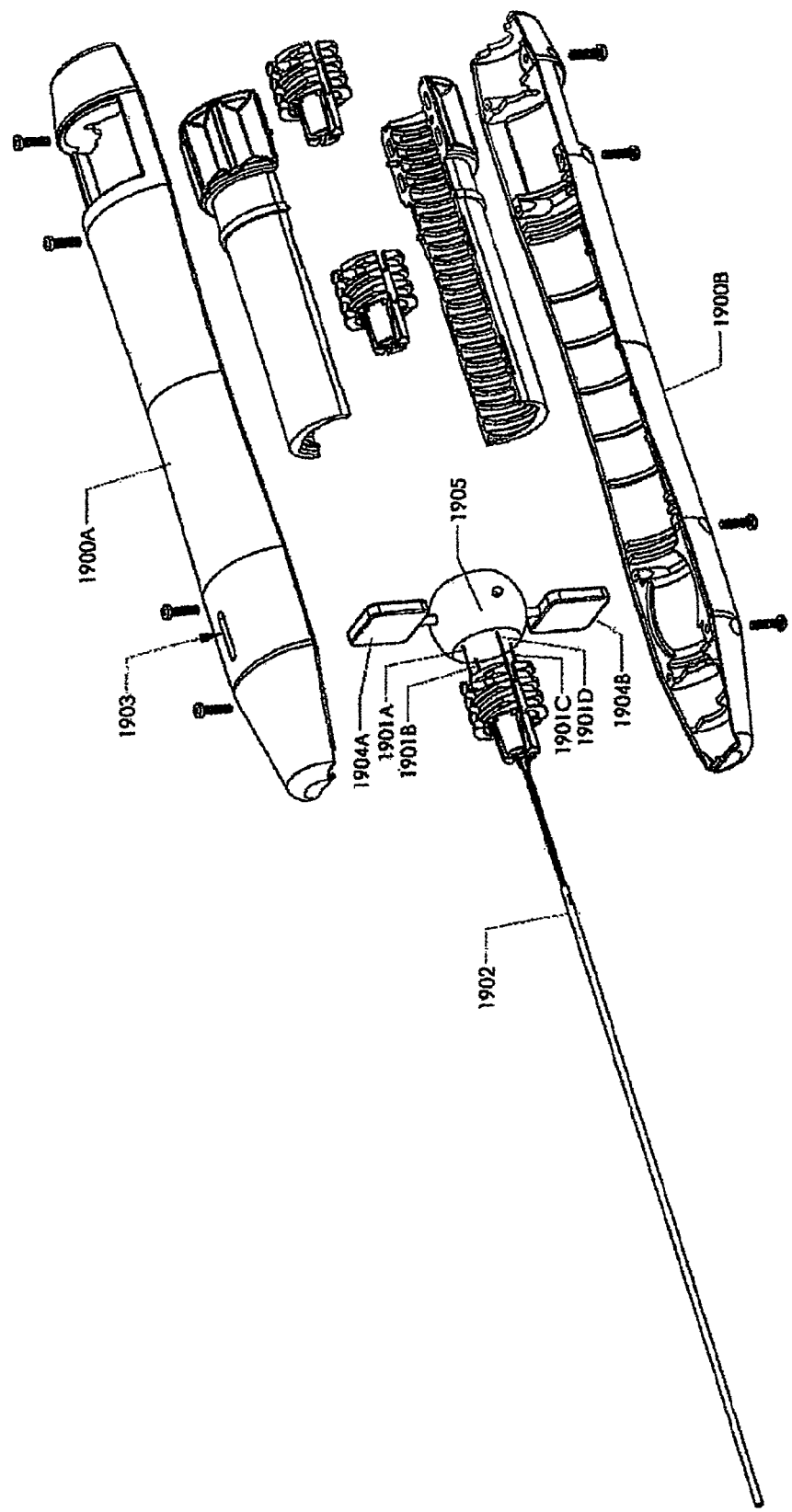
FIG. 19 is a schematic fully-exploded isometric view of an embodiment of a catheter actuation handle assembly according to an embodiment of the invention showing the several component parts for a type of "swash plate" invention configuration.

FIG. 19 is a schematic fully-exploded isometric view of an embodiment of a catheter actuation handle according to an embodiment of the invention showing the several component parts for what can be called a "swash plate" invention configuration that operates on principles similar to the "bilateral swivel" configuration of FIGS. 14 and 15. In FIG. 19, reference numerals 1900A and 1900B identify exterior shell halves, and the screws for securing the two exterior shell halves to each other are shown but not numbered. It will be understood that alternative shell-half connection/fastening systems, for example a "snap-fit" system utilizing correspondingly sized and positioned pins or projections and matching pin holes along the mating edges of two shell halves, can be substituted for the connection system of screws and screw holes illustrated in FIG. 19.

As noted above with respect to FIGS. 17 and 18, FIG. 19 represents a specific application of articulation mechanisms that were generically described earlier in this application for achieving some form of bilateral or multilateral articulation. In FIG. 14, the actuation component is accessed through access portals 1401A, 1401B. In FIG. 19, however, that configuration is replaced with an alternative moveable component-actuation component combination that is capable of actuating a plurality of control/pull wires (which are also referred to herein as "pivot-distal member control wires") 1901A, 1901B, 1901C, 1901D. FIG. 19 illustrates a modified, slot-like type of access port, namely slot 1903. It should be understood, however, that a similarly functioning moveable component-actuation component mechanism could be configured and adapted to fit within previously shown access port designs (such as 1401A, 1401B in FIG. 14). In the FIG. 19 embodiment, swash plates 1904A, 1904B (which function here as the actuation component) are mounted on a centrally-located pivoting member 1905 (that functions here as the moveable component). Pivoting member 1905 would be actuated by a user to simultaneously adjust a plurality of control/pull wires 1901A, 1901B, 1901C, 1901D about a pivot point of pivoting member 1905, which in an embodiment, is centered along the handle axis. With such an embodiment, the user can actuate distally-extending member(s) 1902 in multiple planes according to their orientation about the neutral axis of the distally-extending member(s).

Figure 20:
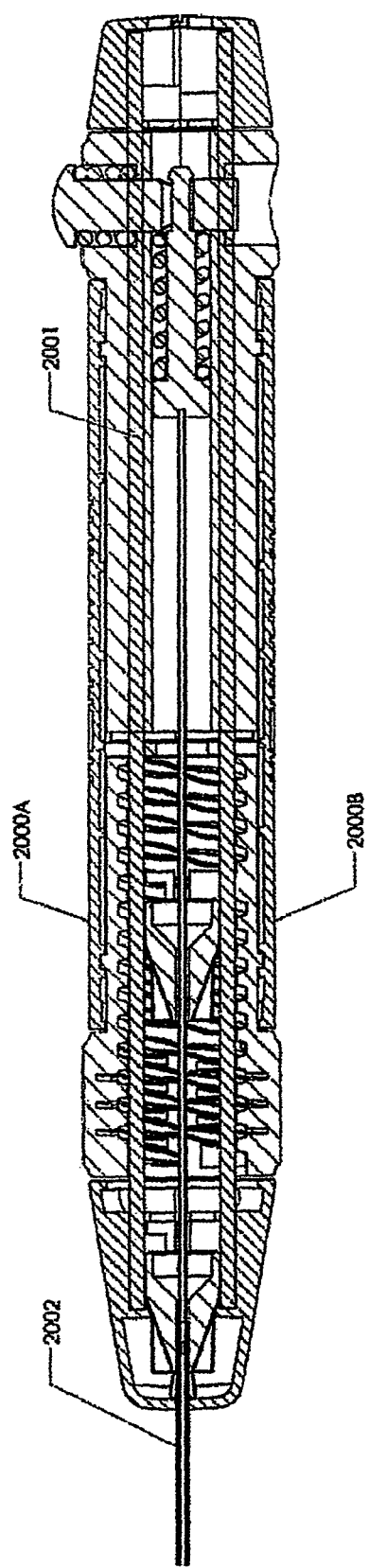
FIG. 20 is a schematic cross-sectional side view of an embodiment of a catheter actuation handle assembly that incorporates component parts for a type of "rapid throw" invention configuration.

FIG. 20 is a schematic cross-sectional side view of an embodiment of the catheter actuation handle that incorporates component parts for a type of "rapid throw" invention configuration. In FIG. 20, reference numerals 2000A and 2000B identify cross-sections of exterior shell halves. This invention embodiment represents a specific application of mechanisms that were generically described earlier in this application for achieving some form of a "rapid thrust" configuration where a distal tip of a distally-extending member can be energized to puncture a septum or body part for carrying out a treatment procedure. More particularly, FIG. 20 shows an "energizable" embodiment of the invention wherein the proximal portion of the actuation handle interior comprises a spring-loaded element 2001, including a compressed spring and a spring-release mechanism (not numbered) actuated via an access port, capable of achieving rapid linear actuation of distally-extending member(s) 2002.

Figure 21:
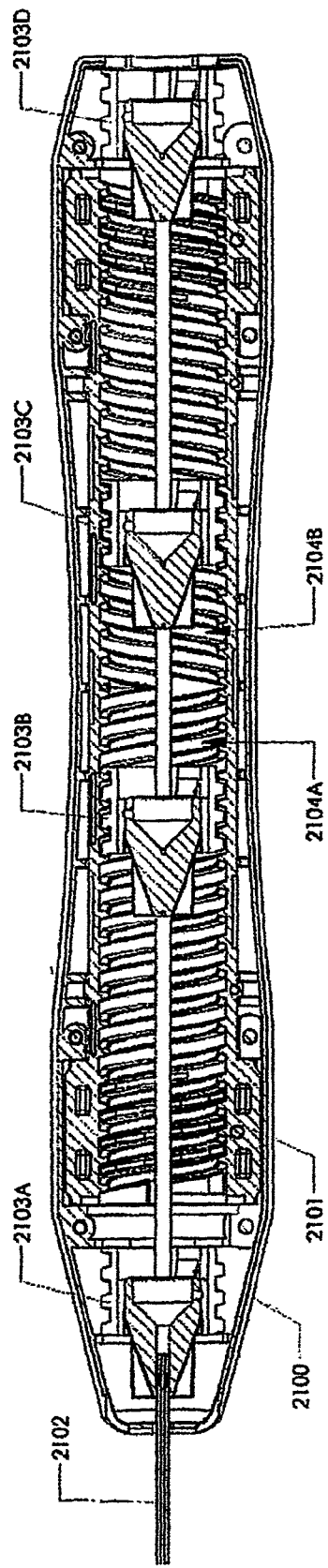
FIG. 21 is a schematic cross-sectional top view of an embodiment of a catheter actuation handle assembly that incorporates "reverse" threading on a portion of the inner surfaces of some portions of the interior shell halves, making it possible to actuate different threadably-engaged drivers for movement in opposing directions with a single rotational action.

FIG. 21 is a schematic cross-sectional top view of an embodiment of a catheter actuation handle that incorporates a combination of regular threading and "reverse" threading on different portions of the inner surfaces of the interior shell halves, thereby making it possible to actuate different moveable drivers 2103B and 2103C for movement in opposing directions with a single rotational action. In FIG. 21, reference numeral 2100 is a sectional view of the exterior shell, and numeral 2102 identifies the distally-extending catheter members. Reference numerals 2103A and 2103D are stationary drivers. In particular, FIG. 21 illustrates configuring an inner surface of interior shell half 2101 to have multiple and differently-oriented thread patterns at discrete locations along its length. These thread pattern variations can include variable thread pitch and/or opposing thread pitch segments, for example thread portions 2104A and 2104B as shown. Such an embodiment allows for simultaneous actuation of two moveable drivers 2103B, 2103C in opposite directions in the interior of the actuation handle using only a single rotation of the interior shell/housing. This type of paired and opposite actuation is advantageous for certain applications, such as for bilateral articulation of two opposing control/pull wires where a first control/pull wire is attached to a first moveable driver 2103B, and a second control/pull wire is attached to a second, oppositely threadably-engaged moveable driver 2103C.

Figure 22:
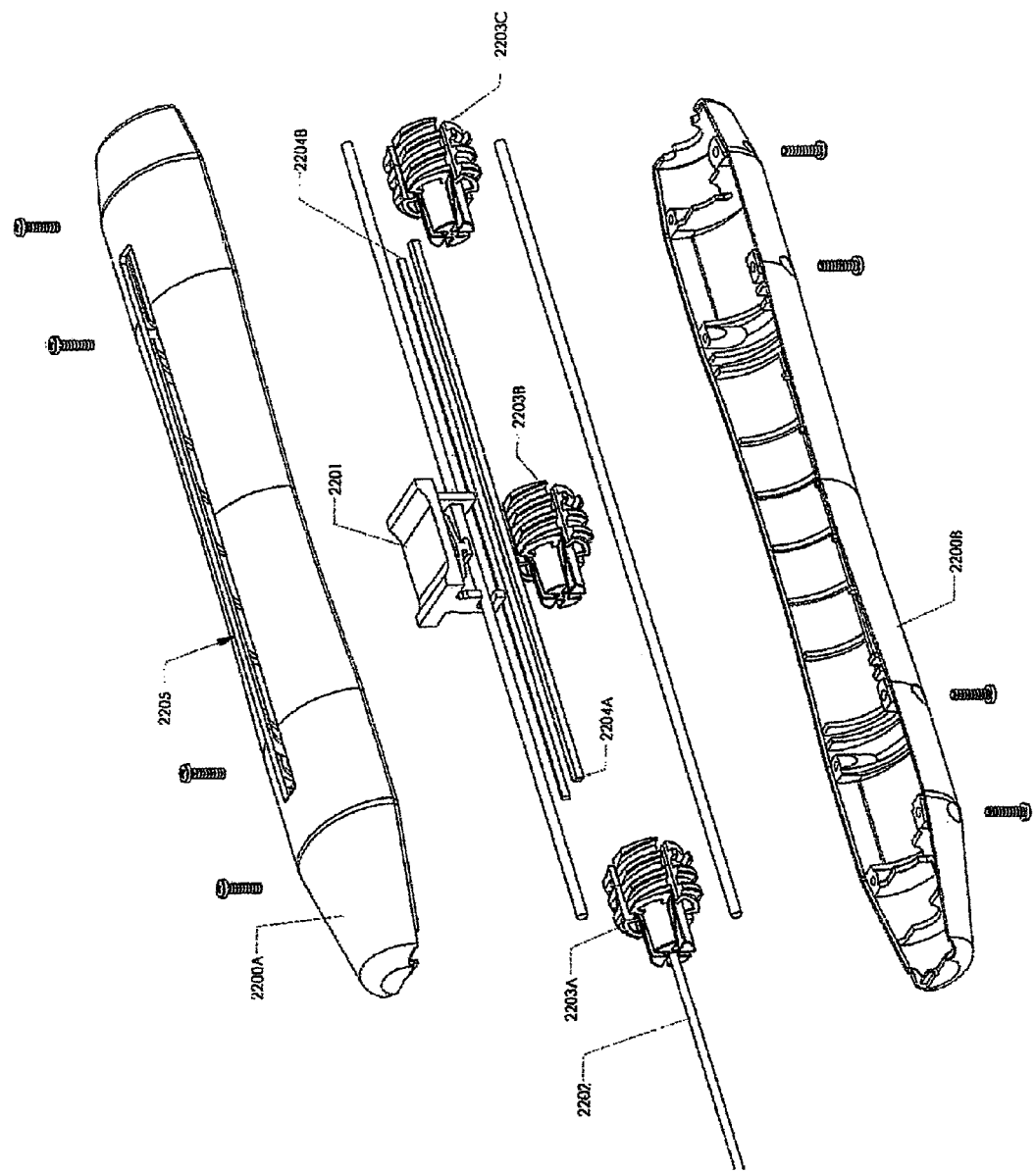
FIG. 22 is a schematic fully-exploded isometric view of an embodiment of a catheter actuation handle assembly according to an embodiment of the invention showing the several component parts for a type of "manual translation" invention configuration.
Figure 23:
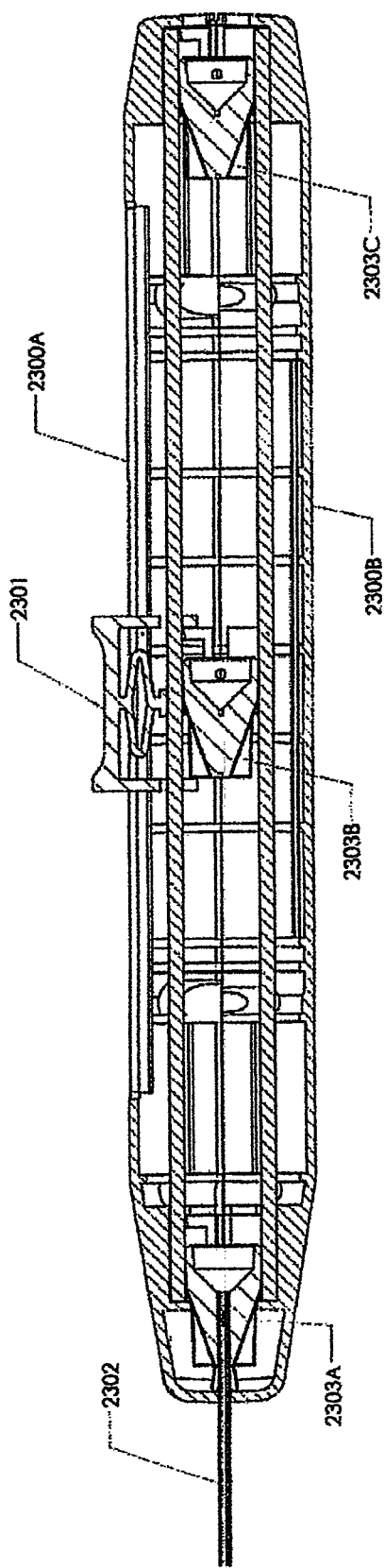
FIG. 23 is a schematic cross-sectional side view of the "manual translation" invention configuration of FIG. 22.

FIG. 22 is a schematic fully-exploded isometric view of an embodiment of a catheter actuation handle according to an embodiment of the invention showing the several component parts for a type of "direct manual translation" invention configuration. In FIG. 22, reference numerals 2203A and 2203C are stationary drivers. In FIG. 22, the screws for securing the two exterior shell halves to each other are shown but not numbered. It will be understood that alternative shell-half connection/fastening systems, for example a "snap-fit" system utilizing correspondingly sized and positioned pins or projections and matching pin holes along the mating edges of two shell halves, can be substituted for the connection system of screws and screw holes illustrated in FIG. 22. FIG. 23 is a schematic cross-sectional side view of the "direct manual translation" invention configuration of FIG. 22 in which reference numerals 2303A and 2303C are the same stationary drivers as drivers 2203A and 2203C, respectively, in FIG. 22.

FIGS. 22 and 23 illustrate configuring the catheter handle for direct manual translation functionality via a slidable positioning button 2201/2301 that slidably rides in an elongated access port or track 2205 in the exterior shell half 2201A. Positioning button 2201/2301 has upper and lower sides. The lower side (located inside the exterior shell cavity) includes a lower-side geometrical feature that can releasably engage a corresponding feature on the surface of moveable driver 2203B/2303B and, thereby, directly transfer movement of the positioning button along track 2205 to any distally-extending member(s) 2202/2302 that are connected to that driver 2203B/2303B. In this embodiment, the user actuates a driver 2203B/2303B via the positioning button 2201/2301 and manually adjusts its location along the elongated track 2205 in at least one of the exterior shell halves 2200A, 2200B/2300A, 2300B. As shown, the positioning button 2201/2301 design utilizes a built-in braking mechanism 2204A, 2204B that pushes the positioning button 2201/2301 against the exterior shell halves 2200A, 2200B/2300A, 2300B to arrest the driver 2203B/2303B when the positioning button is not actively engaged (such as by depressing the positioning button) by the user. Depressing the positioning button 2201/2301 overrides the braking mechanism 2204A, 2204B and allows for longitudinal translation of driver 2203B/2303B along the longitudinal axis of the actuation handle. This embodiment may be utilized over a portion of the actuation handle's length, and in conjunction with any of the other embodiments previously described. This embodiment of the invention can utilize the two exterior shell halves 2200A, 2200B and does not necessarily require or use the interior shell halves (comprising the interior housing) shown in previously described embodiments.

Figure 24:
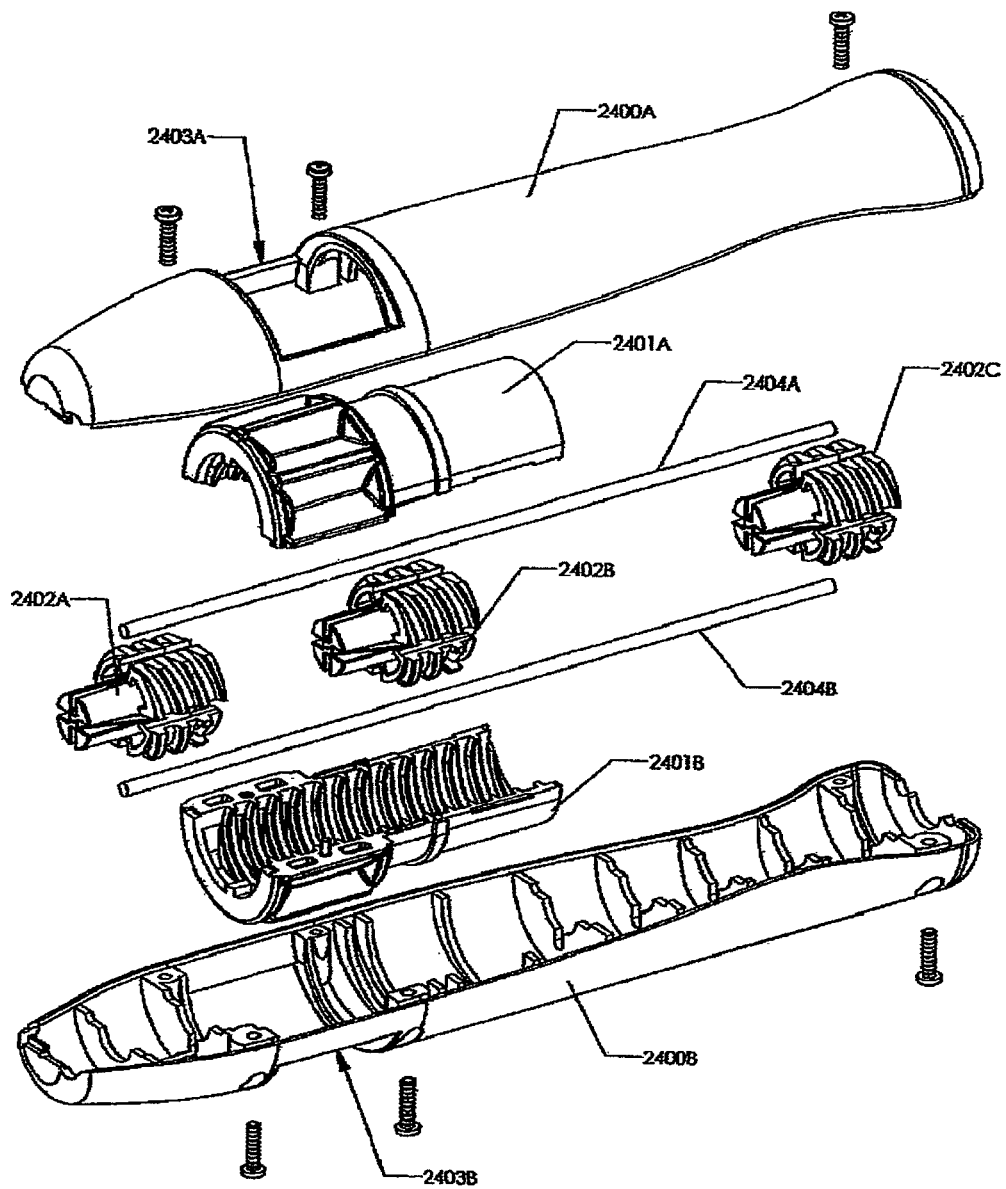
FIG. 24 is a schematic fully-exploded isometric view of an embodiment of a catheter actuation handle assembly according to an embodiment of the invention showing an alternate outer housing configuration that enables a "single-action" actuation function.

FIG. 24 is a schematic fully-exploded isometric view of an embodiment of a catheter actuation handle according to an embodiment of the invention showing an alternate outer housing configuration that enables a "single-action" function. In FIG. 24, reference numerals 2402A and 2402C are stationary drivers, and reference numerals 2404A and 2404B are guide rails. The screws for securing the two exterior shell halves

Figure 25:
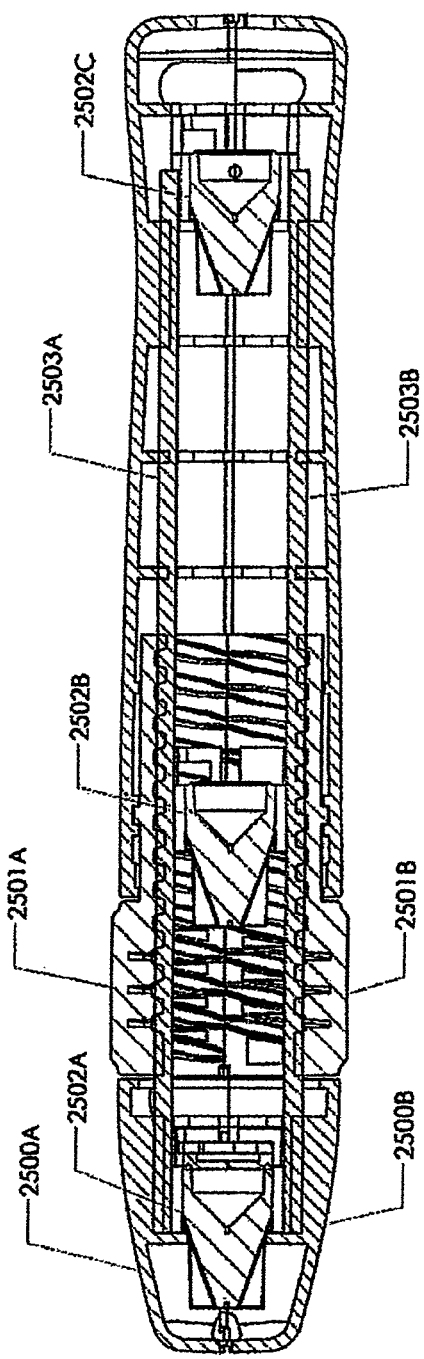
FIG. 25 is schematic cross-sectional side view of the "single-action" invention configuration of FIG. 24.

2400A and 2400B to each other are shown but not numbered. It will be understood that alternative shell-half connection/fastening systems, for example a "snap-fit" system utilizing correspondingly sized and positioned pins or projections and matching pin holes along the mating edges of two shell halves, can be substituted for the connection system of screws and screw holes illustrated in FIG. 24. FIG. 25 is a schematic cross-sectional side view of the "single-action" invention configuration of FIG. 24 in which reference numerals 2502A and 2502C are the same stationary drivers as drivers 2402A and 2402C, respectively, in FIG. 24. Similarly, guide rails 2503A and 2503B in FIG. 25 correspond, respectively, to guide rails 2404A and 2404B in FIG. 24.

More particularly, FIGS. 24 and 25 show an alternative set of exterior shell halves 2400A, 2400B/2500A, 2500B housing a moveable component-actuation component combination comprising the moveable driver 2402B/2502B and an associated actuation component. The actuation component for this invention embodiment consists of interior shell halves 2401A, 2401B/2501A, 2501B (comprising an interior shell/housing) having threaded interior surfaces at least along a portion of the interior surfaces with that threading engaging matching threads on the primary outer surface of driver 2402B/2502B. The interior shell halves (interior shell/housing) are accessed for movement through access ports 2403A, 2403B, similar to some previously described configurations. This design utilizes the same type of modular configuration (based on largely interchangeable component parts that can be readily assembled for use, disassembled after use, and, if desired, re-used in a new and perhaps different catheter actuation handle configuration) as previously described embodiments of the invention. The catheter actuation handle configuration of FIGS. 24 and 25, however, has certain advantageous ergonomics and a simplified construct for applications in which only a single moveable driver is required to provide the desired control of distally-extending members.

Figure 26:
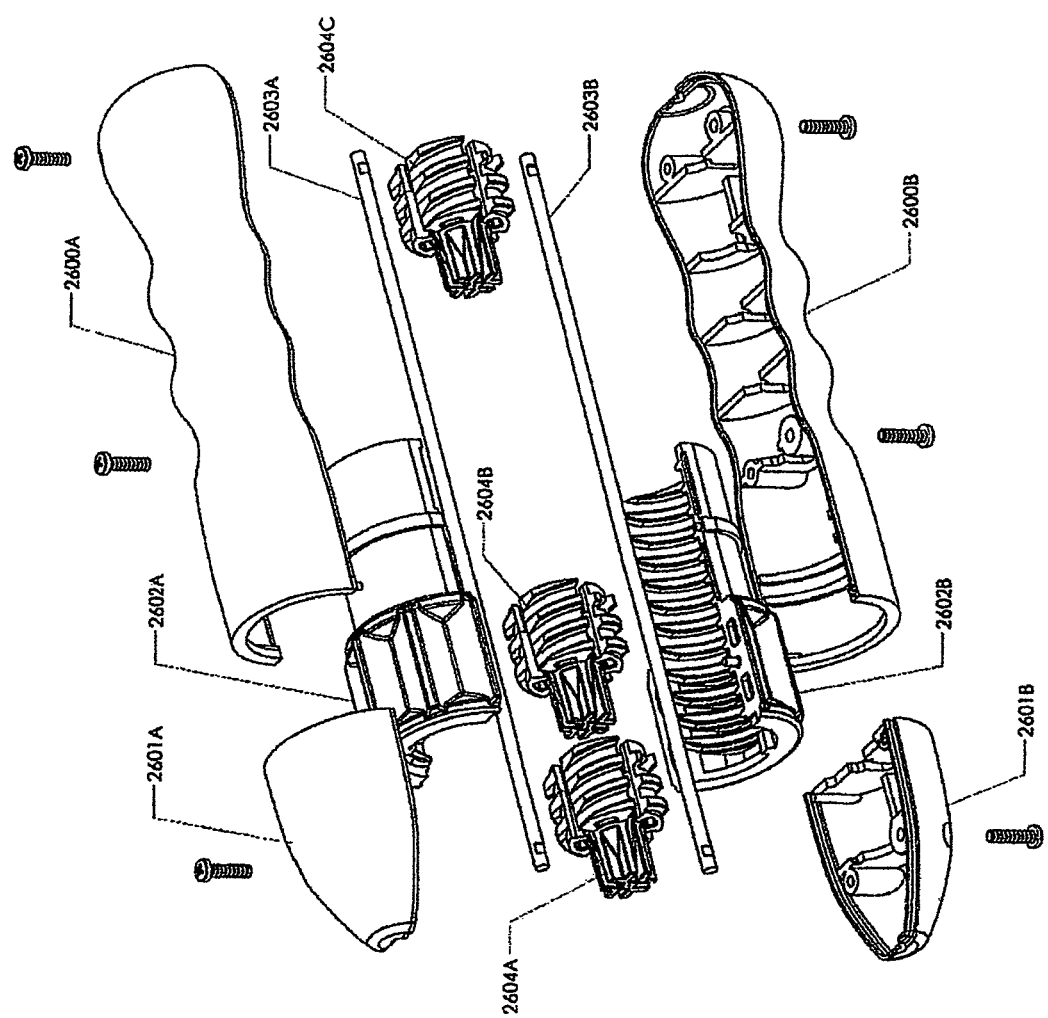
FIG. 26 is a schematic fully-exploded isometric view of an embodiment of a catheter actuation handle assembly showing the several component parts for a type of "cantilevered nose" invention configuration that also enables "single-action" actuation.
Figure 27:
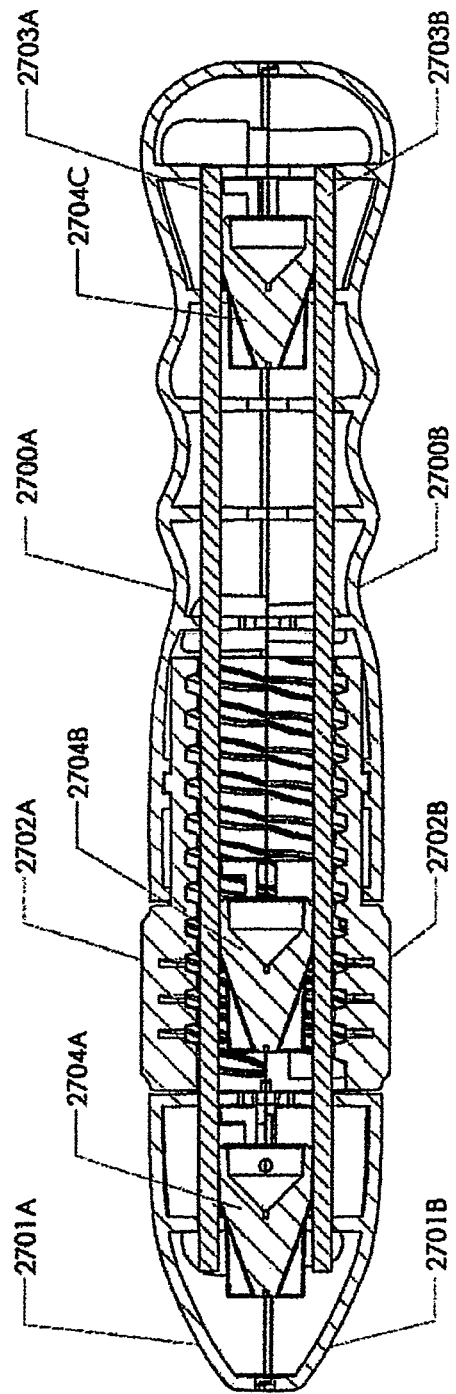
FIG. 27 is a schematic cross-sectional side view of the "cantilevered nose" invention configuration of FIG. 26.

FIG. 26 is a schematic fully-exploded isometric view of an embodiment of a catheter actuation handle showing the several component parts for a type of "cantilevered nose" invention configuration that also enables "single-action" behavior. In FIG. 26, reference numeral 2604C is a proximal-end stationary driver. The screws for securing exterior shell halves 2601A and 2601B to each other are shown but not numbered. It will be understood that alternative shell-half connection/fastening systems, for example a "snap-fit" system utilizing correspondingly sized and positioned pins or projections and matching pin holes along the mating edges of two shell halves, can be substituted for the connection system of screws and screw holes illustrated in FIG. 26. FIG. 27 is a schematic cross-sectional side view of the "cantilevered nose" invention configuration of FIG. 26 in which reference numeral 2704C is the same proximal-end stationary driver as driver 2604C in FIG. 26.

More particularly, FIGS. 26 and 27 show an alternate embodiment with similar benefits to those illustrated and described for the single-action design of FIGS. 24 and 25. In this version, however, a separate distal nose segment is formed by combining two additional exterior shell halves 2601A, 2601B/2701A, 2701B, in order to form a second, distal segment of the exterior shell/housing. The separate nose segment of the exterior shell/housing can contain a stationary driver 2604A/2704A in a position distal relative to the actuation handle's primary actuation mechanism. The distal exterior shell halves 2601A, 2601B/2701A, 2701B that comprise the nose segment are connected to the proximal exterior shell segment, comprised of exterior shell halves 2600A, 2600B/2700AC, 2700B, via guide rods 2603A, 2603B/2703A, 2703B such that the assembled nose segment is rigidly held in place, but is separated from the distal end of the proximal exterior shell segment by a small distance (which typically might be about the width of a human thumb). This spatial separation between the nose segment and the proximal segment of the exterior shell/housing constitutes a full circumferential communication aperture for accessing the interior shell. A threadably-engaged moveable driver 2604B/2704B can be actuated by rotating the interior shell halves 2602A, 2602B/2702A, 2702B (which comprise the interior shell), which are accessible to the user via the circumferential access port. This actuation mechanism is utilized for mechanical output and actuation of distally-extending members as previously described. In addition to improved ergonomics of size and shape, however, this separate nose segment design allows for full, uninterrupted circumferential access to the interior shell, which may be preferred by some users and/or for some applications of the actuation handle.

It will be apparent to those skilled in the art that other changes and modifications may be made in the above-described catheter actuation handle apparatus and the methods of assembling and using that apparatus without departing from the scope of the invention herein, and it is intended that all matter contained in the above description shall be interpreted in an illustrative and not a limiting sense.

Having described our invention, what we claim is:

1. A catheter actuation handle assembly adapted to manipulate one or more distally-extending members that connect to the catheter handle and extend from the handle to locations distal from the handle for realizing translation, articulation and/or rotation of these distally-extending members using a combination of components comprising at least a moveable component that is connected to a distally-extending member and is actuated by an associated actuation component that can be manually manipulated, said handle assembly comprising:

at least a pair of mating exterior shell halves, each exterior shell half having an exterior shell outer surface and an exterior shell inner surface, the pair of exterior shell halves being mateable with one another to form a generally cylindrically-shaped actuation handle housing having a cross-sectional shape selected from circular and ovular, and the housing defines an exterior shell cavity and a handle longitudinal axis;

at least a moveable component positioned inside the exterior shell cavity whereby the moveable component is enabled for linear movement along, and/or rotational movement about, the longitudinal axis, by engagement with one or more actuation components of the assembly;

at least a connection between the moveable component and a distally-extending member; and, one or more access ports through the actuation handle housing providing access into the exterior shell cavity for manipulating the moveable component and/or the actuation component from outside the actuation handle housing;

also wherein:

the actuation component comprises a pair of mating interior shell halves forming a cylindrically-shaped interior shell segment that is sized to fit inside and rotate within the exterior shell cavity;

the moveable component comprises at least a first moveable driver;

threading along an interior shell inner surface engages corresponding threading along an outer surface of the moveable driver whereby rotation of the interior shell segment via an associated access port causes linear movement of the moveable driver along the handle longitudinal axis; and the handle assembly further comprises corresponding circumferential rib projections along the inner surfaces of the exterior shell halves and also along the outer surfaces of the interior shell halves to facilitate positioning and rotation of the interior shell inside the exterior shell cavity, and one or more knob features along the outer surface of the interior shell at locations where the knob features align with and project at least partly into or through an access port.

2. A catheter actuation handle assembly according to claim 1 wherein the handle assembly further comprises at least first and second stationary drivers of substantially the same size and shape as the moveable driver that are positioned inside the exterior shell cavity, one located proximal of and the other being distal of the interior shell segment containing the moveable driver, and also includes at least a pair of guide rails positioned in guide rail slots on opposite sides of the proximal stationary driver, and extending through corresponding guide rail slots of the moveable driver and to corresponding guide rail slots of the distal stationary driver to constrain rotation of the moveable driver during rotation of the interior shell segment.

3. A catheter actuation handle assembly according to claim 2 wherein the handle assembly further comprises at least first and second stationary drivers of substantially the same size and shape as the moveable driver that are positioned inside the exterior shell cavity, one located proximal of and the other being distal of the interior shell segment containing the moveable driver, and the assembly also comprises circumferential rib projections along the inner surfaces of the exterior shell halves at their proximal and distal ends that define pockets for accommodating the stationary drivers.

4. A catheter actuation handle assembly according to claim 1 wherein the moveable driver comprises a threaded driver end having a first diameter with circumferential threading along the outer surface and axially-oriented guide rail slots intersecting the threading, and an unthreaded protrusion driver end having a second diameter, smaller than the first diameter, and with axially-oriented control wire slots along the outer surface.

5. A catheter actuation handle assembly according to claim 4 further wherein the threaded driver end includes an end face with a recess sized and shaped to receive sealing and locking elements.

6. A catheter actuation handle assembly according to claim 1 wherein the handle assembly includes a moveable driver-distal member control wire that connects at least one moveable driver to a distally-extending member.

7. A catheter actuation handle assembly according to claim 1 wherein the handle assembly includes at least one stationary driver located within the exterior shell cavity together with a stationary driver-distal member control wire that connects at least one of the stationary drivers to a distally-extending member.

8. A catheter actuation handle assembly according to claim 1 wherein the handle assembly includes at least one stationary driver located within the exterior shell cavity together with a stationary driver-distal member control wire that connects at least one of the stationary drivers to a distally-extending member, and also a moveable driver-distal member control wire that connects at least one moveable driver to a distally-extending member.

9. A catheter actuation handle assembly according to claim 1 wherein the handle assembly includes a moveable driver-distal member control wire that connects at least one moveable driver to a distally-extending member, and at least one stationary driver connected to a distally-extending member.

10. A catheter actuation handle assembly according to claim 1 wherein the handle assembly includes a moveable driver-distal member control wire that connects at least one moveable driver to a distally-extending member, and a guide sleeve that houses at least a portion of the moveable driver-distal member control wire that is in the exterior shell cavity.

11. A catheter actuation handle assembly according to claim 1 wherein the moveable driver comprises a threaded driver end having a first diameter with circumferential threading along the outer surface and axially-oriented guide rail slots intersecting the threading, and also an unthreaded protrusion driver end having a second diameter, smaller than the first diameter, and with axially-oriented control wire slots along the outer surface, and further wherein a moveable driver-distal member control wire passes through one of the driver's control wire slots and connects the moveable driver to a distally-extending member.

12. A catheter actuation handle assembly according to claim 1 wherein the handle assembly is sized and shaped to be held in and controlled by a single human hand.

13. A catheter actuation handle assembly according to claim 1 wherein the exterior shell halves, or the interior shell halves or both are symmetrical relative to the corresponding mating shell half.

14. A catheter actuation system comprising a catheter handle assembly according to claim 1 in combination with a fluid/flush line and a fluid source that provides fluid communication between a fluid source that is external to the actuation handle housing and a location inside the exterior shell cavity.

15. A catheter actuation system according to claim 14 wherein the fluid/flush line provides a fluid communication to the proximal end of a catheter lumen of a distally-extending member.

16. A catheter actuation handle assembly according to claim 1 further comprising at least a distally-extending member connected to a moveable driver wherein movement of the moveable driver by means of the actuation component has resulted in translation, articulation or rotation of the distally-extending member into an actuated configuration different from a pre-actuation configuration.

17. A catheter actuation handle assembly adapted to manipulate one or more distally-extending members that connect to the catheter handle and extend from the handle to locations distal from the handle for realizing translation, articulation and/or rotation of these distally-extending members using a combination of components comprising at least a moveable component that is connected to a distally-extending member and is actuated by an associated actuation component that can be manually manipulated, said handle assembly comprising:

at least a pair of mating exterior shell halves, each exterior shell half having an exterior shell outer surface and an exterior shell inner surface, the pair of exterior shell halves being mateable with one another to form a generally cylindrically-shaped actuation handle housing having a cross-sectional shape selected from circular and ovular, and the housing defines an exterior shell cavity and a handle longitudinal axis;

at least a moveable component positioned inside the exterior shell cavity whereby the moveable component is enabled for linear movement along, and/or rotational movement about, the longitudinal axis, by engagement with one or more actuation components of the assembly;

at least a connection between the moveable component and a distally-extending member; and, one or more access ports through the actuation handle housing providing access into the exterior shell cavity for manipulating the moveable component and/or the actuation component from outside the actuation handle housing;

also wherein:

the actuation component comprises a pair of mating interior shell halves forming a cylindrically-shaped interior shell segment that is sized to fit inside and rotate within the exterior shell cavity;

the moveable component comprises at least a first moveable driver;

threading along an interior shell inner surface engages corresponding threading along an outer surface of the moveable driver whereby rotation of the interior shell segment via an associated access port causes linear movement of the moveable driver along the handle longitudinal axis;

at least a first stationary driver of substantially the same size and shape as the moveable driver is positioned inside the exterior shell cavity proximal or distal of the interior shell segment containing the moveable driver, with a connection between the stationary driver and a distally-extending member;

corresponding circumferential rib projections along the inner surfaces of the exterior shell halves and also along the outer surfaces of the interior shell halves facilitate positioning and rotation of the interior shell inside the exterior shell cavity; and, one or more knob features are located along the outer surface of the interior shell at locations where the knob features align with and project at least partly into or through an access port.

18. A catheter actuation handle assembly according to claim 17 wherein the handle assembly further comprises at least first and second stationary drivers of substantially the same size and shape as the moveable driver that are positioned inside the exterior shell cavity, one located proximal of and the other being distal of the interior shell segment containing the moveable driver.

19. A catheter actuation handle assembly according to claim 17 wherein the handle assembly further comprises at least first and second stationary drivers of substantially the same size and shape as the moveable driver that are positioned inside the exterior shell cavity, one located proximal of and the other being distal of the interior shell segment containing the moveable driver, and also includes at least a pair of guide rails positioned in guide rail slots on opposite sides of the proximal stationary driver, and extending through corresponding guide rail slots of the moveable driver and to corresponding guide rail slots of the distal stationary driver to constrain rotation of the moveable driver during rotation of the interior shell segment.

20. A catheter actuation handle assembly according to claim 19 wherein the handle assembly includes a moveable driver-distal member control wire that connects at least one moveable driver to a distally-extending member, and at least one stationary driver connected to a distally-extending member.

21. A catheter actuation handle assembly according to claim 17 wherein the handle assembly further comprises at least first and second stationary drivers of substantially the same size and shape as the moveable driver that are positioned inside the exterior shell cavity, one located proximal of and the other being distal of the interior shell segment containing the moveable driver, and the assembly also comprises circumferential rib projections along the inner surfaces of the exterior shell halves at their proximal and distal ends that define pockets for accommodating the stationary drivers.

22. A catheter actuation handle assembly according to claim 17 wherein the moveable driver comprises a threaded driver end having a first diameter with circumferential threading along the outer surface and axially-oriented guide rail slots intersecting the threading, and an unthreaded protrusion driver end having a second diameter, smaller than the first diameter, and with axially-oriented control wire slots along the outer surface.

23. A catheter actuation handle assembly according to claim 22 further wherein the threaded driver end includes an end face with a recess sized and shaped to receive sealing and locking elements.

24. A catheter actuation handle assembly according to claim 17 wherein the handle assembly includes a moveable driver-distal member control wire that connects at least one moveable driver to a distally-extending member.

25. A catheter actuation handle assembly according to claim 17 wherein the handle assembly includes a stationary driver-distal member control wire that connects at least one of the stationary drivers to a distally-extending member.

26. A catheter actuation handle assembly according to claim 17 wherein the handle assembly includes a stationary driver-distal member control wire that connects at least one of the stationary drivers to a distally-extending member, and also a moveable driver-distal member control wire that connects at least one moveable driver to a distally-extending member.

27. A catheter actuation handle assembly according to claim 17 wherein the handle assembly includes a moveable driver-distal member control wire that connects at least one moveable driver to a distally-extending member, and a guide sleeve that houses at least a portion of the moveable driver-distal member control wire that is in the exterior shell cavity.

28. A catheter actuation handle assembly according to claim 17 wherein the moveable driver comprises a threaded driver end having a first diameter with circumferential threading along the outer surface and axially-oriented guide rail slots intersecting the threading, and also an unthreaded protrusion driver end having a second diameter, smaller than the first diameter, and with axially-oriented control wire slots along the outer surface, and further wherein a moveable driver-distal member control wire passes through one of the driver's control wire and connects the moveable driver to a distally-extending member.

29. A catheter actuation handle assembly according to claim 17 wherein the handle assembly is sized and shaped to be held in and controlled by a single human hand.

30. A catheter actuation handle assembly according to claim 17 wherein the exterior shell halves, or the interior shell halves or both are symmetrical relative to the corresponding mating shell half.

31. A catheter actuation system comprising a catheter handle assembly according to claim 17 in combination with a fluid/flush line and a fluid source that provides fluid communication between a fluid source that is external to the actuation handle housing and a location inside the exterior shell cavity.

32. A catheter actuation system according to claim 31 wherein the fluid/flush line provides a fluid communication to the proximal end of a catheter lumen of a distally-extending member.

33. A catheter actuation handle assembly according to claim 17 further comprising at least a distally-extending member connected to a moveable driver wherein movement of the moveable driver by means of the actuation component has resulted in translation, articulation or rotation of the distally-extending member into an actuated configuration different from a pre-actuation configuration.

34. A catheter actuation handle assembly adapted to manipulate one or more distally-extending members that connect to the catheter handle and extend from the handle to locations distal from the handle for realizing translation, articulation and/or rotation of these distally-extending members using a combination of components comprising at least a moveable component that is connected to a distally-extending member and is actuated by an associated actuation component that can be manually manipulated, said handle assembly comprising:

- at least a pair of mating exterior shell halves, each exterior shell half having an exterior shell outer surface and an exterior shell inner surface, the pair of exterior shell halves being mateable with one another to form a generally cylindrically-shaped actuation handle housing having a cross-sectional shape selected from circular and ovular, and the housing defines an exterior shell cavity and a handle longitudinal axis;
- at least a moveable component positioned inside the exterior shell cavity whereby the moveable component is enabled for linear movement along, and/or rotational movement about, the longitudinal axis, by engagement with one or more actuation components of the assembly;
- at least a connection between the moveable component and a distally-extending member; and,
- one or more access ports through the actuation handle housing providing access into the exterior shell cavity for manipulating the moveable component and/or the actuation component from outside the actuation handle housing;
- also wherein:
    the actuation component comprises a pair of mating interior shell halves forming a cylindrically-shaped interior shell segment that is sized to fit inside and rotate within the exterior shell cavity;
    the moveable component comprises at least first and second moveable drivers;
    threading along an interior shell inner surface engages corresponding threading along outer surfaces of the moveable drivers whereby rotation of the interior shell segment via an associated access port causes linear movement of the moveable drivers along the handle longitudinal axis, and the first and second moveable drivers are of substantially the same size and shape, and each is associated with a driver-distal member control wire that connects the moveable driver to a distally-extending member; and
    one or more knob features are located along the outer surface of the interior shell at locations where the knob features align with and project at least partly into or through an access port.

35. A catheter actuation handle assembly according to claim 34 further wherein each of the moveable drivers is located in a separate, independently rotatable interior shell segment such that it can be actuated independently of the other moveable drivers.

36. A catheter actuation handle assembly according to claim 35 wherein the handle assembly further includes an actuation component associated with each moveable driver, each actuation component comprising a pair of mating interior shell halves forming a cylindrically-shaped interior shell segment that is sized to fit inside and rotate within the exterior shell cavity such that threading along an interior shell inner surface engages corresponding threading along an outer surface of the associated moveable driver whereby rotation of the interior shell segment via an associated access port causes linear movement of the driver along the handle longitudinal axis.

37. A catheter actuation handle assembly according to claim 35 wherein the handle assembly further includes an actuation component that comprises a pair of mating interior shell halves forming a cylindrically-shaped interior shell segment that is sized to fit inside and rotate within the exterior shell cavity such that first threading along a first portion of the interior shell inner surface engages corresponding threading along an outer surface of the first moveable driver, and second threading of a different orientation direction and/or a different pitch than the first threading along a second portion of the interior shell inner surface engages corresponding threading along an outer surface of the second moveable driver, whereby rotation of the interior shell segment housing the first and second moveable drivers via an associated access port results in linear movement of both moveable drivers but in different directions or at different rates of movement.

38. A catheter actuation handle assembly according to claim 34 further wherein each of the moveable drivers is located in a separate, independently rotatable interior shell segment such that it can be actuated independently of the other moveable drivers, and the assembly also comprises a knob feature along the outer surface of each interior shell segment that houses a moveable driver at locations where the knob feature aligns with and projects at least partly into or through an access port.

39. A catheter actuation handle assembly according to claim 34 further wherein each of the moveable drivers is located in a separate, independently rotatable interior shell segment such that it can be actuated independently of the other moveable drivers, and also wherein a slotted support washer is positioned between at least two of the separate interior shell segments with slots sized and located to accommodate a pair of guide rails that extend between the most proximal and the most distal drivers.

40. A catheter actuation handle assembly according to claim 34 further wherein each of the moveable drivers is located in a separate, independently rotatable interior shell segment such that it can be actuated independently of the other moveable drivers, and also wherein a distal-end stationary driver is positioned distal of the most distal of the moveable drivers, a proximal-end stationary driver is positioned proximal of the most proximal of the moveable drivers, and a mid-body stationary driver is positioned between the most distal moveable driver and the most proximal moveable driver.

41. A catheter actuation handle assembly according to claim 34 further wherein each of the moveable drivers is located in a separate, independently rotatable interior shell segment such that it can be actuated independently of the other moveable drivers, and also wherein a distal-end stationary driver is positioned distal of the most distal of the moveable drivers, a proximal-end stationary driver is positioned proximal of the most proximal of the moveable drivers, and a mid-body stationary driver is positioned between the most distal moveable driver and the most proximal moveable driver, and also slotted support washers are positioned between the interior shell segment housing the mid-body stationary driver and the distal and proximal interior shell segments housing, respectively, the distal moveable driver and the proximal moveable driver, each slotted support washer having slots sized and located to accommodate a pair of guide rails that extend between the most proximal and the most distal drivers.

42. A catheter actuation handle assembly according to claim 34 wherein the handle assembly includes a moveable driver-distal member control wire that connects at least one moveable driver to a distally-extending member.

43. A catheter actuation handle assembly according to claim 34 wherein the handle assembly includes at least one stationary driver located within the exterior shell cavity together with a stationary driver-distal member control wire that connects at least one of the stationary drivers to a distally-extending member.

44. A catheter actuation handle assembly according to claim 34 wherein the handle assembly includes at least one stationary driver located within the exterior shell cavity together with a stationary driver-distal member control wire that connects at least one of the stationary drivers to a distally-extending member, and also a moveable driver-distal member control wire that connects at least one moveable driver to a distally-extending member.

45. A catheter actuation handle assembly according to claim 34 wherein the handle assembly includes a moveable driver-distal member control wire that connects at least one moveable driver to a distally-extending member, and at least one stationary driver connected to a distally-extending member.

46. A catheter actuation handle assembly according to claim 34 wherein the handle assembly includes a moveable driver-distal member control wire that connects at least one moveable driver to a distally-extending member, and a guide sleeve that houses at least a portion of the moveable driver-distal member control wire that is in the exterior shell cavity.

47. A catheter actuation handle assembly according to claim 34 wherein the moveable driver comprises a threaded driver end having a first diameter with circumferential threading along the outer surface and axially-oriented guide rail slots intersecting the threading, and also an unthreaded protrusion driver end having a second diameter, smaller than the first diameter, and with axially-oriented control wire slots along the outer surface, and further wherein a moveable driver-distal member control wire passes through one of the driver's control wire slots and connects the moveable driver to a distally-extending member.

48. A catheter actuation handle assembly according to claim 34 wherein the handle assembly is sized and shaped to be held in and controlled by a single human hand.

49. A catheter actuation handle assembly according to claim 34 wherein the exterior shell halves, or the interior shell halves or both are symmetrical relative to the corresponding mating shell half.

50. A catheter actuation system comprising a catheter handle assembly according to claim 34 in combination with a fluid/flush line and a fluid source that provides fluid communication between a fluid source that is external to the actuation handle housing and a location inside the exterior shell cavity.

51. A catheter actuation system according to claim 50 wherein the fluid/flush line provides a fluid communication to the proximal end of a catheter lumen of a distally-extending member.

52. A catheter actuation handle assembly according to claim 34 further comprising at least a distally-extending member connected to a moveable driver wherein movement of the moveable driver by means of the actuation component has resulted in translation, articulation or rotation of the distally-extending member into an actuated configuration different from a pre-actuation configuration.

* * * * *